(12) United States Patent
Goldstein et al.

(10) Patent No.: US 7,166,472 B2
(45) Date of Patent: Jan. 23, 2007

(54) METHOD FOR THE IDENTIFICATION OF AGENTS THAT INHIBIT OR PROMOTE CATARACTS AND USES THEREOF

(75) Inventors: Lee E. Goldstein, Marblehead, MA (US); Ashley I. Bush, Sommerville, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/983,780

(22) Filed: Nov. 9, 2004

(65) Prior Publication Data

US 2005/0084918 A1    Apr. 21, 2005

Related U.S. Application Data

(62) Division of application No. 10/344,860, filed as application No. PCT/US00/25975 on Sep. 22, 2000.

(60) Provisional application No. 60/226,125, filed on Aug. 18, 2000.

(51) Int. Cl.
G01N 33/00 (2006.01)
G01N 21/76 (2006.01)

(52) U.S. Cl. .......................... 436/86; 436/172

(58) Field of Classification Search ................ 436/73, 436/86, 164, 172; 435/448; 530/350, 402
See application file for complete search history.

(56) References Cited

U.S. PATENT DOCUMENTS 4,778,815 A * 10/1988 Cash .......................... 514/359

FOREIGN PATENT DOCUMENTS

EP       0 397 437 A1   5/1990
WO       WO 99/09981 A1  3/1999

OTHER PUBLICATIONS

Harding, J.J. Can cataract be prevented? (1999) Eye, 13:454-456.*
Harding, J.J. Can drugs or micronutrients prevent cataract? (2001) Drugs & Aging 18:473-86.*
Asbell et al. Age-related cataract. (2005) Lancet 365:599-609.*
Pritchard et al. Making better drugs: Decision gates in non-clinical drug development. (2003) Nature Reviews Drug Discovery 2:542-553.*
Lin et al. UV-B-induced secondary conformational changes in lens a-crystallin (1999) J. Photochem. Photobiol. B: Biology 49:29-34.*
Aquilina, J.A., et al., "Elucidation of a Novel Polypeptide Cross-Link Involving 3-Hydroxykynurenine," *Biochemistry* 38:11455-11464, American Chemical Society (Aug. 1999).
Augusteyn, R.C. and Koretz, J.F., "Hypothesis: A possible structure for α-crystallin," *FEBS Lett.* 222:1-5, Elsevier Science Publishers B.V. (1987).
Barker, L.R., et al., "Common Problems Associated with Impaired Vision: Cataracts and Age-Related Macular Degeneration," in *Principles of Ambulatory Medicine*, 4th Ed., Barker, L.R., et al., eds., Williams and Wilkins Publishing, pp. 1416-1419 (1995).
Balaji, M., et al., "Copper levels in human mixed, nuclear brunescence, and posterior subcapsular cataract," *Br. J. Ophthalmol.* 76:668-669, BMJ Publishing Group (1992).
Bando, M., et al., "Spectrophotometric Estimation of 3-OH L-Kynurenine O-β-Glucoside in the Human Lens," *J. Biochem.* (Tokyo) 89:103-109, The Japanese Biochemical Society (1981).
Benavente, M.G. and Truscott, R.J.W., "Modification of Proteins by 3-Hydroxyanthranilic Acid: The Role of Lysine Residues," *Arch. Biochem. Biophys.* 290:451-457, Academic Press, Inc. (1991).
Benedek, G.B., "Cataract as a Protein Condensation Disease: The Proctor Lecture," *Invest. Ophthalmol. Vis. Sci.* 38:1911-1921, Association For Research In Vision And Ophthalmology (1997).
Beebe, D.C., "Nuclear cataracts and Nutrition: Hope for Intervention Early and Late in Life," *Invest. Ophthalmol. Vis. Sci.* 39:1531-1534, Association For Research In Vision And Ophthalmology (1998).
Bhat, S.P., et al., "αB-crystallin exists as an independent protein in the heart and in the lens," *Eur. J. Biochem.* 202:775-781, Springer International on behalf of the Federation of European Biochemical Societies (1991).
Bhuyan, K.C., et al., "Lipid Peroxidation in Cataract of the Human," *Life Sci.* 38:1463-1471, Pergamon Press, Ltd. (1986).
Bindoli, A., et al., Biochemical and Toxicological Properties of the Oxidation Products of Catecholamines, *Free Radic. Biol. Med.* 13:391-405, Pergamon Press, Ltd. (1992).
Brown, N.A.P., et al., "Nutrition supplements and the eye," *Eye* 12:127-133, Nature Publishing Group (1998).
Carrell, R.W., and Lomas, D.A., "Conformational disease," *The Lancet* 350:134-138, Lancet Publishing Group (1997).
Carver, J.A., et al., "α-Crystallin: molecular chaperone and protein surfactant," *Biochem. Biophys. Acta* 1204:195-206, Elsevier Science B.V. (1994).
Cekic, O., "Effect of cigarette smoking on copper, lead, and cadmium accumulation in human lens," *Br. J. Ophthalmol.* 82:186-188, BMJ Publishing Group (1998).
Chen, Y.C., et al., "Molecular Evidence for the Involvement of Alpha Crystallin in the Colouration/Crosslinking of Crystallins in Age-related Nuclear Cataract," *Exp. Eye Res.* 65:835-840, Academic Press, Ltd. (1997).
Chiarugi, A., et al., "The kynurenine metabolic pathway in the eye: studies on 3-hydroxykynurenine, a putative cataractogenic compound," *FEBS Lett.* 453:197-200, Elsevier Science B.V. on behalf of the Federation of European Biochemical Societies (Jun. 1999).

(Continued)

*Primary Examiner*—Long V. Le
*Assistant Examiner*—Christine E. Foster
(74) *Attorney, Agent, or Firm*—Sterne, Kessler, Goldstein & Fox, P.L.L.C.

(57) ABSTRACT

Described are methods for the identification of agents useful in the treatment or prevention of cataracts. Also described are methods for the identification of agents that may inadvertently promote or accelerate the formation of cataracts, and methods of treating or preventing injuries to or diseases of the ocular lens, retina and/or macula. More specifically, the invention describes methods for the identification of pharmacological agents useful in treating cataracts by inhibiting the cross-linking of eye lens proteins.

22 Claims, 10 Drawing Sheets

OTHER PUBLICATIONS

Christen, S., et al., "Antioxidant activities of some tryptophan metabolites: Possible implication for inflammatory diseases," *Proc. Natl. Acad. Sci. USA* 87:2506-2510, National Academy Press (1990).

Cook, C.S., and McGahan, M.C., "Copper concentration in cornea, iris, normal, and cataractous lenses and intraocular fluids of vertebrates," *Curr. Eye Res.* 5:69-76, IRL Press, Ltd. (1986).

Dilley, K.J., and Pirie, A., "Changes to the Proteins of the Humans Lens Nucleus In Cataract," *Exp. Eye Res.* 19:59-72, Academic Press (1974).

Dillon, J., "UV-B as a pro-aging and pro-cataract factor," *Documenta Ophtalmologica* 88:339-344, Kluwer Academic Publishers (1995).

Dykens, J.A., et al., "Oxidative reactivity of the tryptophan metabolites 3-hydroxyanthranilate, cinnabarinate, quinolinate and picolinate," *Biochem. Pharmacol.* 36:211-217, Pergamon Journals,Ltd. (1987).

Fay et al., "Diseases of the Visual System," in *Cecil's Textbook of Medicine*, 21st Ed., Goldman, L. and Bennett, J.C., eds., W.B. Saunders Company, pp. 2231-2232 (Oct. 1999).

Fecondo, J.V., and Augusteyn, R.C., "Superoxide Dismutase, Catalase and Glutathione Peroxidase in the Human Cataractous Lens," *Exp. Eye Res.* 36:15-23, Academic Press Inc. (London), Ltd. (1983).

Flanagan, E.M., et al., "Neurotoxin Quinolinic Acid Is Selectively Elevated in Spinal Cords of Rats with Experimental Allergic Encephalomyelitis," *J. Neurochem.* 64:1192-1196, Raven Press, Ltd. (1995).

Goldstein, L.E., et al., "3-Hydroxykynurenine and 3-Hydroxyanthranilic Acid Generate Hydrogen Peroxide and Promote $\alpha$-Crystallin Cross-Linking by Metal Ion Reduction," *Biochemistry* 39:7266-7275, American Chemical Society (Jun. 2000).

Goshima, N., et al., "3-Hydroxykynurenine as O2 Scavenger in the Blowfly, Aldrichina Grahami," Biochim. *Biophys. Res. Comm.* 139:666-672, Academic Press, Inc. (1986).

Groenen, P.J.T.A., et al., "Structure and modifications of the junior chaperone $\alpha$-crystallin: From lens transparency to molecular pathology," *Eur. J. Biochem.* 225:1-19, Springer International on behalf of the Federation of European Biochemical Societies (1994).

Gutteridge, J.M.C., "Bleomycin-detectable iron in knee-joint synovial fluid from arthritic patients and its relationship to the extracellular antioxidant activities of caeruloplasmin, transferrin and lactoferrin," *Biochem. J.* 245:415-421, Portland Press On Behalf Of The Biochemical Society (1987).

Halliwell, B., and Gutteridge, J.M.C., "Oxygen toxicity, oxygen radicals, transition metals and disease," *Biochem J.* 219:1-14, Royal Society of London (1984).

Halliwell, B., et al., "Metal ions and oxygen radical reactions in human inflammatory joint disease," *Phil. Trans. R. Soc. Lond. B*: 311:659-671, Royal Society of London (1985).

Harding, J.J., "Conformational Changes in Human Lens Proteins in Cataract," *Biochem. J.* 129:97-100, Portland Press On Behalf Of The Biochemical Society (1972).

Harding, J.J., "Cataract, Alzheimer's disease, and other conformational diseases," *Curr. Opin. Ophthalmol.* 9:10-13, Rapid Science Publishers (1998).

Heyes, M.P., et al., "A mechanism of quinolinic acid formation by brain in inflammatory neurological disease," *Brain* 116:1425-1450, Oxford University Press (1993).

Heyes, M.P., et al., "Poliovirus induces indoleamine-2,3-dioxygenase and quinolinic acid synthesis in macaque brain," *FASEB. J.* 6:2977-2989, Federation of American Societies for Experimental Biology (1992).

Hiraku, Y., et al., "Metal-mediated oxidative damage to cellular and isolated DNA by certain tryptophan metabolites," *Carcinogenesis* 16:349-356, Oxford University Press (1995).

Hood, B.D., et al., "Human Lens Coloration and Aging," *J. Biol. Chem.* 274:32547-32550, The American Society for Biochemistry and Molecular Biology, Inc. (Nov. 1999).

Horwitz, J., "$\alpha$-Crystallin can function as a molecular chaperone," *Proc. Natl. Acad. Sci. USA* 89:10449-10453, National Academy Press (1992).

Huang, X., et al., "The A$\beta$ Peptide of Alzheimer's Disease Directly Produces Hydrogen Peroxide through Metal Ion Reduction," *Biochemistry* 38:7609-7616, American Chemical Society (Published on Web—May 1999).

Kuznezova, L.E., "Mutagenic Effect of 3-Hydroxykynurenine and 3-Hydroxyanthranilic Acid," *Nature* 22:484-485, Macmillan (Journals), Ltd. (1969).

Lévay, G., et al., "Formation of DNA Adducts and Oxidative Base Damage by Copper Mediated Oxidation of Dopamine and 6-Hydroxydopamine," *Exp. Neurol.* 146:570-574, Academic Press (1997).

Luthra, M., and Balasubramanian, D., "3-Hydroxykynurenine and 3-Hydroxyanthranilic Acid May Act as Endogenous Antioxidants in the Eye Lens," *Exp. Eye Res.* 55:641-643, Academic Press, Ltd. (1992).

Malina, H.Z., and Martin, X.D., "Deamination of 3-hydroxykynurenine in bovine lenses: a possible mechanism of cataract formation in general," *Grafe's Arch. Clin. Exp. Ophthalmol.* 233:38-44, Springer-Verlag (1995).

Malina, H.Z., and Martin, X.D., "Xanthurenic acid derivative formation in the lens is responsible for senile cataract in humans," *Graefe's Arch. Clin. Exp. Ophthalmol.* 234:723-730, Springer-Verlag (1996).

Mathias, R.T., et al., "Cell to Cell Communication and pH in the Frog Lens," *J. Gen. Physiol.* 98:1085-1103, The Rockefeller University Press (1991).

Micelli-Ferrari, T., et al., "Role of lipid peroxidation in the pathogenesis of myopic and senile cataract," *Br. J. Ophthalmol.* 80:840-843, BMJ Publishing Group (1996).

Munn, D.H., et al., "Prevention of Allogeneic Fetal Rejection by Tryptophan Catabolism," *Science* 281:1191-1193, American Association for the Advancement of Science (1998).

Nath, R., et al., "Accumulation of Copper & Inhibition of Lactate Dehydrogenase Activity in Human Senile Cataractous Lens," *Indian J. Exp. Biol.* 7:25-26, Council of Scientific & Industrial Research. New Dehli (1969).

Obara, Y., "The Oxidative Stress in the Cataract Formation," *Nippon Ganka Gakkai Zasshi* 99:1303-1341, Nihon Ganka Gakkai (1995), Abstract only considered.

Ogawa, T., et al., "Kynurenine pathway abnormalities in Parkinson's disease," *Neurology* 42:1702-1706, Lippincott, Williams & Wilkins (1992).

Okuda, S., et al., "Hydrogen peroxide-mediated neuronal cell death induced by an endogenous neurotoxin, 3-hydroxykynurenine," *Proc. Natl. Acad. Sci. USA* 93:12553-12558, National Academy Press (1996).

Okuda, S., et al., "3-Hydroxykynurenine, an Endogenous Oxidative Stress Generator, Causes Neuronal Cell Death with Apoptotic Features and Region Selectivity," *J. Neurochem.* 70:299-307, Lippincott-Raven Publishers (1998).

Pearson, S.J., and Reynolds, G.P., "Increased brain concentrations of a neurotoxin, 3-hydroxykynurenine, in Huntington's disease." *Neurosci. Lett.* 144:199-201, Elsevier Scientific Publishers Ireland, Ltd. (1992).

Ramachandran, S., et al., "Radio-isotopic Determination of Hydrogen Peroxide in Aqueous Humor and Urine," *Exp. Eye Res.* 53:503-506, Academic Press, Ltd. (1991).

Rácz, P., and Erdöhelyi, Å., "Cadmium, Lead and Copper Concentrations in Normal and Senile Cataractous Human Lenses," *Ophthalmic. Res.* 20:10-13, S. Karger AG, Basel (1988).

Rasi, V., et al., "Inorganic Element Concentrations in Cataractous Human Lenses," *Ann. Ophthalmol.* 24:459-464, American Society of Contemporary Ophthalmology (1992).

Reynolds, G.P., and Pearson, S.J., "Increased brain 3-hydroxykynurenine in Huntington's disease," *The Lancet* 2:979-980, Lancet Publishing Group (1989).

Rogers, K.M., and Augusteyn, R.C., "Glutathione Reductase in Normal and Cataractous Human Lenses," *Exp. Eye Res.* 27:719-721, Academic Press, Inc. (1978).

Sanni, L.A., et al., "Dramatic Changes in Oxidative Tryptophan Metabolism along the Kynurenine Pathway in Experimental Cerebral and Noncerebral Malaria," *Am. J. Pathol. 152*:611-619, American Society for Investigative Pathology (1998).

Sarder, A.M., et al., "Increased Concentrations of the Neurotoxin 3-Hydroxykynurenine in the Frontal Cortex of HIV-1-Positive Patients," *J. Neurochem. 64*:932-935, Raven Press (1995).

Spector, A., "Oxidation and cataract," *Ciba Found. Symp. 106*:48-64, Pitman Publishing, Ltd. (1984).

Srivastava, V.K., et al., "Role of trace elements in senile cataract," *Acta Ophthalmol. (Copenh.) 70*:839-841, Scriptor Publishers Aps (1992).

Starkebaum, G., and Harlan, J.M., "Endothelial Cell Injury Due to Copper-catalyzed Hydrogen Peroxide Generation from Homocysteine," *J. Clin. Invest. 77*:1370-1376, The American Society for Clinical Investigation, Inc. (1986).

Stutchbury, G.M., and Truscott, R.J.W., "The Modification of Proteins by 3-Hydroxykynurenine," *Exp. Eye Res. 57*:149-155, Academic Press, Ltd. (1993).

Sun, T-X., et al., "Conformational and Functional Differences between Recombinant Human Lens ÿA-and αB-Crystallin," *J. Biol. Chem. 272*:6220-6225, The American Society for Biochemistry and Molecular Biology, Inc. (1997).

Takikawa, O., et al., "Regulation of indoleamine 2,3-dioxygenase, the first enzyme in UV filter biosynthesis in the human lens," *Adv. Exp. Med. Biol. 467*:241-245, Kluwer Academic/Plenum Publishers (Nov. 1999).

Taylor, M.W., and Feng, G., "Relationship between interferon-y, indoleamine 2,3-dioxygenase. and tryptophan catabolism," *FASEB. J. 5*:2516-2522, The Federation of American Societies for Experimental Biology (1991).

Tomoda, A., et al., "Mechanism of Coloration of Human Lenses Induced by Near-Ultraviolet-Photo-Oxidized 3-Hydroxykynurenine," *Ophthalmic Res. 22*:152-159, Karger AG, Basel (1990).

Van Heyningen, R., "Assay of Fluorescent Glucosides in the Human Lens," *Exp. Eye Res. 15*:121-126, Academic Press (1973).

Van Heyningen, R., "Fluorescent Glucoside in the Human Lens," *Nature 230*:393-394, Macmillan Journals, Ltd. (1971).

Varma, S.H., "Scientific basis for medical therapy of cataracts by antioxidants," *Am. J. Clin. Nutr. 53*:335S-345S, American Society of Clinical Nutrition (1991).

Wood, A.M., and Truscott, R.J.W, "UV Filters in Human Lenses: Tryptophan Catabolism," *Exp. Eye Res. 56*:317-325, Academic Press, Ltd. (1993).

Wood, A.M., and Truscott, R.J.W., Ultraviolet Filter Compounds in Human Lenses: 3-Hydroxykynurenine Glucoside Formation, *Vision Res. 34*:1369-1374, Elsevier Science, Ltd. (1994).

Yoshida, R., et al., "Induction of indoleamine 2,3-dioxygenase in mouse lung during virus infection," *Proc. Natl. Acad. Sci. USA 76*:4084-4086, National Academy Press (1979).

Zigler, Jr., J.S., and Goosey, J.D., "Photosensitized oxidation in the ocular lens: Evidence for photosensitizers endogenous to the human lens," *Photochem. Photobiol. 33*:869-874, Pergamon Press, Ltd. (1981).

International Search Report for International Application No. PCT/US00/25975 mailed on Dec. 27, 2000.

U.S. Appl. No. 10/344,860, Bush et al., filed Feb. 19, 2003, mailed Mar. 3, 2005.

Zanger, M. and Gennaro, A. R., "Structure-Activity Relationship and Drug Design," in *Remington's Pharmaceutical Sciences, Sixteenth Edition*, Osol, A., ed., Mack Publishing, pp. 420-425 (1980).

* cited by examiner

METHOD FOR THE IDENTIFICATION OF AGENTS THAT INHIBIT OR PROMOTE CATARACTS AND USES THEREOF

CROSS REFERENCE TO RELATED APPLICATIONS

The present application is a divisional of U.S. patent application Ser. No. 10/344,860, which has a 371(e) date of Jul. 18, 2003 and is a 371 of International Patent Application No. PCT/US00/25975, filed Sept. 22, 2000, which claims the benefit of U.S. Provisional Patent Application No. 60/226,125, filed Aug. 18, 2000.

BACKGROUND OF THE INVENTION

Treatment of cataracts is the single largest expense item in the U.S. Medicare budget, costing over $5 billion a year and affecting about 8 million Americans. There are over twenty different causes of cataracts and, although surgical treatment of the disorder is effective, there are no more conservative or less expensive therapeutic alternatives at this time. Additionally, many patients throughout the world do not have access to surgical treatments for this disorder.

A clear understanding of the pathogenesis of the disorder, which affects the same population of people as does Alzheimer's disease, is lacking. Cataracts and Alzheimer's disease may be linked by a rise in lenticular copper concentrations as a stochastic consequence of aging which is a common risk factor for both disorders. Several groups have observed that copper levels are elevated on the order of 50-fold in the cataract-affected eye and in the cataractous lens itself (Cekic, O., Br. J. Opthal. 82:186–188 (1998)).

A substantial body of evidence has accumulated suggesting that oxidative processes play a prominent role in the cascade of biochemical events leading to cataract formation (Spector, A., Ciba Foundation Symposium 106:48–62 (1984)), macular degeneration and retinitis pigmentosa. These oxidative processes are the end result, the "downstream" final common biochemical pathway, of cellular damage. The chemical reactions that involve redox-active metals (such as copper and iron) and oxygen, result in free radical species which are known to be toxic to most cells in living tissue, including the eye. The end-products of these chemical reactions are known as reactive oxygen species (ROS) and include hydrogen peroxide, superoxide anion, singlet oxygen, and the highly reactive and toxic hydroxyl radical. ROS are known to toxically interact with cellular proteins, nucleic acids, lipid membranes, and other essential cellular constituents, resulting in cross-linking and/or degradation and ultimately leading to cell damage and death. As a result of these processes, the functional integrity of the tissues so affected is compromised. Over the course of a lifetime of exposure to ROS, biological systems deteriorate, ultimately leading to degenerative or frank disease states.

In cataracts, the long-lived lenticular crystallin proteins accumulate post-translational chemical modifications (e.g., proteolytic fragmentation, glycation, amino acid racemization, disulfide and covalent cross-linking, carbonylation, and methionine oxidation, among others) and form high molecular weight protein cross-linked aggregates within the lens, specifically within the cytosol. Many of these changes are suspected to be the direct result of exposure to ROS and may lead to profound alterations in protein conformation. Thus, during cataractogenesis, α-crystallin undergoes a conformational transition from a soluble protein found in the transparent lens to a colored, insoluble, highly cross-linked aggregate (Chen, Y. C. et al., Exp. Eye Res. 65: 835–840 (1997); Harding, J. J., Biochem J. 129: 97–100 (1972); Harding, J. J., Curr. Opin. Ophthalmol. 9: 10–13 (1998); Dilley, K. J., and Pirie, A., Exp. Eye Res. 19: 59–72 (1974)).

As the crystallin proteins are not susceptible to protein clearance mechanisms in the fiber cells in the interior of the lens, the modified and aggregated crystallin protein masses accumulate ("condense"—Benedek, G. B., Invest. Ophthal. Vis. Sci. 38:1911–1921 (1997)) in an increasingly disordered fashion, leading one prominent researcher to place cataracts within the framework of conformational diseases (Carrell, R. W. and Lomas, D. A., Lancet 350:134–138 (1997)) such as Alzheimer's disease, sickle-cell anemia, and Creutzfeld-Jakob disease (Harding, J., J. Curr. Opin. Ophthalmol. 9:10–13 (1998)). This oxidatively engendered protein cross-linkage and aggregation results in progressive opacification of the lens (the sine qua non of cataracts) with decreased light transmission to the retina, and increased light scattering within the lens itself. The combination of these processes leads to blindness.

Evidence suggesting that oxidative processes are involved in cataractoge nesis is consistent with clinical evidence demonstrating increased hydrogen peroxide levels in the aqueous humor of cataractous eyes, increased lipid peroxidation markers such as malonidaldehyde in aged and cataractous lenses, and decreased antioxidant in cataractous lens (Bhuyan, K. C. et al., Life Sci. 38: 1463–1471 (1986); Micelli-Ferrari, T. et al., Br. J. Ophthalnol. 80: 840–843 (1996); Spector, A., Ciba Foundation Symposium 106:48–64 (1984); Ramachandran, S. et al., Exp. Eye Res. 53: 503–506 (1991)). As noted above, numerous studies have also demonstrated elevated levels of total copper in cataractous lenses (Cekic, O., Br. J. Ophthalmol. 82: 186–188 (1998); Balaji, M. et al., Br. J. Ophthalmol. 76: 668–669 (1992); Rasi, V. et al., Ann. Ophthalmol. 24: 459–464 (1992); Srivastava, V. K. et al., Acta Ophthalmol. (Copenh.) 70: 839–841 (1992); Racz, P., and Erdohelyi, A., Ophthalmic. Res. 20: 10–13 (1988); Cook, C. S., and McGahan, M. C., Curr. Eye Res. 5: 69–76 (1986); Nath, R. et al., Indian J. Exp. Biol. 7: 25–26 (1969); Srivastava, V. K. et al., Acta Ophthalmol., 70:839–841 (1992); Obara, Y., Nippon Ganka Gakkai Zasshi, 99:1303–1341 (1995)). This finding is important as Cu(II) is a co-factor in generating potentially damaging ROS, such as hydrogen peroxide and superoxide, which may foster protein aggregation as noted in other systems (e.g., the Alzheimer's disease $A\beta_{1-42}$ protein) (Huang, X. et al., Biochem. 38: 7609–7616 (1999)). Further, decreases in the level of antioxidant defense enzymes such as glutathione reductase, glutathione peroxidase and superoxide dismutase, as well as decreases in total glutathione and corresponding increases in oxidized glutathione, have been observed (Rogers, K. M., and Augusteyn, R. C., Exp. Eye Res. 27: 719–721 (1978); Fecondo, J. V., and Augusteyn, R. C., Exp. Eye Res. 36: 15–23 (1983); Bhuyan, K. C. et al., Life Sci. 38:1463–1471 (1986)).

Clinical efficacy of antioxidants such as vitamins A, C and E in delaying cataract formation provide further suggestive evidence of oxidative mechanisms in this disorder (Brown, N. A. P. et al., Eye 12:127–133 (1998); Beebe, D. C., Invest. Ophthalmol. Vis. Sci., 39:1531–1534 (1998)). Additionally, antioxidants such as ascorbate, vitamin E and pyruvate have been shown to protect against cataract formation in mice (Shambhu, D. V., Am. J. Clin. Nutr. 53:335S-345S (1991)).

Redox-active transition metals are involved in harmful oxidative processes associated with a number of disorders such as Huntington's Disease (Reynolds, et al., Lancet 2:979–980 (1989); Pearson et al., *Neurosci. Lett.* 144:199–201 (1992)); Parkinson's disease (Ogawa et al., *Neurology* 42:1702–1706 (1992)); HIV encephalopathy (Sarder et al., *J. Neurochem.* 64:932–935 (1995)); cerebral malaria (Sanni et al., *Am. J. Pathol.* 152:611–619 (1998)); and fetomaternal tolerance (Sanni et al., *Science* 281:1191–1193 (1998)). The possible significance of redox-active metal in cataractogenesis is highlighted by the well-known clinical observation of rapid cataract formation following introduction of intraocular foreign bodies containing transitional metals such as copper or iron.

Thus, there is a need to find therapeutic agents that will inhibit or disrupt the various processes that are involved in cataract formation and development. Assay methods are needed that may be used to screen the many existing compounds, and compounds yet to be created, for their ability to disrupt the oxidation reactions and related cross-linking reactions that lead to the formation of cataracts, or to find molecules that retard or delay the progression of vision loss due to such cataract-causing reactions.

SUMMARY OF THE INVENTION

The invention describes methods for the identification of potential pharmacological agents to be used in the prevention and/or treatment of cataracts and for the identification of agents that may inadvertently promote or accelerate the formation of cataracts.

More specifically the invention describes a method for the identification of a pharmacological agent to be used in the treatment or prevention of cataracts, wherein said agent results in either decreasing or preventing cross-linking of a target protein, said method comprising:

(a) adding a reducible redox-active metal source to a first target protein sample comprising an auto-oxidizing kynurenine pathway metabolite;

(b) allowing said first target protein sample to incubate for an amount of time sufficient to allow cross-linking of said target protein;

(c) adding said reducible redox-active metal source to a second target protein sample comprising an auto-oxidizing kynurenine pathway metabolite, said second sample additionally comprising a candidate pharmacological agent;

(d) allowing said second sample to incubate for the same amount of time as said first sample;

(e) determining the amount of target protein cross-linking by said first sample and said second sample; and (f) comparing the amount of target protein cross-linking produced by said first sample to the amount of target protein cross-linking produced by said second sample;

whereby a decrease in the amount of target protein cross-linking produced by said second sample as compared to said first sample indicates that said candidate pharmacological agent is useful in the treatment or prevention of cataracts.

The amount of cross-linked target protein in said first and said second sample may be determined by any method suitable for measuring cross-linked proteins. The preferred methods for determining the amount of cross-linked target protein in said first and said second sample is selected from the group consisting of Western blotting, filtration assay, aggregation/sedimentation, turbidometry, fluorometry, spectrophotometry, and lens or retinal culture combined with light microscopy or light scattering technology. Any protein capable of cross-linking may be used as the target protein in the assay of the present invention. The preferred target protein is α-crystallin and the preferred reducible redox-active metal source comprises Cu(II) and/or Fe(III). The preferred auto-oxidizing kynurenine pathway metabolite is an o-aminophenol compound selected from the group consisting of 3-hydroxykynurenine (3-HK), 3-hydroxyanthranilic acid (3-HAA), xanthurenic acid (XA) or other aminophenol compounds.

In one embodiment of the invention, two or more different test candidate agents are simultaneously evaluated for an ability to alter target protein cross-linking.

In another embodiment of the invention, the target protein samples are incubated under ultraviolet B irradiation.

In another embodiment of the present invention, the assay method may be used to determine whether an agent causes or accelerates the cross-linking of a target protein. In such a method, an increase in said target protein cross-linking indicates potential for causing or accelerating cataract formation. This method comprises:

(a) adding a reducible redox-active metal source to a first target protein sample comprising an auto-oxidizing kynurenine pathway metabolite;

(b) allowing said first target protein sample to incubate for an amount of time sufficient to allow cross-linking of said target protein;

(c) adding said reducible redox-active metal source to a second target protein sample comprising an auto-oxidizing kynurenine pathway metabolite, said second sample additionally comprising a candidate pharmacological agent;

(d) allowing said second sample to incubate for the same amount of time as said first sample;

(e) determining the amount of target protein cross-linking by said first sample and said second sample; and (f) comparing the amount of target protein cross-linking produced by said first sample to the amount of target protein cross-linking produced by said second sample;

whereby, an increase in the amount of target protein cross-linking produced by the second sample as compared to the first sample indicates that the agent may cause or accelerate the formation of cataracts.

The amount of cross-linked target protein in said first and said second sample is determined, in part, by the target protein's ability to form cross-links among a mixture of target protein molecules.

Assay methods for determining an increase or decrease in cross-linking depend upon the use of any assay that allows the separation of cross-linked from non-cross-linked target proteins. Preferred assay methods for measuring cross-linking of target protein are selected from the group consisting of Western blotting, filtration assay, aggregation/sedimentation, turbidometry, fluorometry, spectrophotometry, and lens or retinal culture combined with light microscopy or light scattering technology. The preferred target protein is α-crystallin and the preferred reducible redox-active metal source comprises Cu(II) and/or Fe(III). The preferred auto-oxidizing kynurenine pathway metabolite is an o-aminophenol compound selected from the group consisting of 3-hydroxykynurenine, 3-hydroxyanthranilic acid, and xanthurenic acid or other aminophenol compounds.

In one embodiment of the invention, two or more different test candidate agents are simultaneously evaluated for an ability to alter target protein cross-linking.

In another embodiment of the invention, the target protein samples are incubated under ultraviolet B irradiation.

Thus, the assay method of the present invention may be used to evaluate any compound for its propensity to promote cataracts in a mammal. Knowledge of a compound's ability to promote cataracts allows the establishment of dangerous dosage levels for pharmaceutical compositions, environmental pollutants, cosmetics, chemical products, radiation, etc.

In another embodiment of the invention, the assay method of the present invention may be used to evaluate redox-active transition metal chelators suitability as pharmaceutical agents useful in preventing or treating injury to or disease of the ocular lens, retina and/or macula, such as age-related cataracts, in a mammal. The redox-active transition metal chelator may then be administered to a mammal in a therapeutically effective amount. The preferred redox-active transition metal chelator is selected from the group consisting of bathocuproine, bathophenanthroline, triethylenetetramine, diethylenetriaminepentaacetic acid, penicillamine, clioquinol, desferroxamine, and derivatives, homologues, analogues, prodrugs or pharmaceutically acceptable salts or esters thereof. Among the most preferred redox-active transition metal chelators are hydrophobic, i.e., lipophilic, chelators that can cross the plasma membrane and permeate the cytosol, such as clioquinol or a derivative, homologue, analogue, prodrug or pharmaceutically acceptable salt or ester thereof.

BRIEF DESCRIPTION OF THE FIGURES

FIG. 2A is a graph showing the ability of kynurenine pathway metabolites to reduce Cu(II) and Fe(III) to Cu(I) and Fe(II), respectively. FIG. 2B shows the ability of the Cu(II) chelator triethylenetetramine (TETA) and the Fe(III) chelator diethylenetriaminepentaacetic acid (DTPA) to abolish the respective reduction signals of the kynurenine pathway metabolites. Values represent the mean±SD for three independent measurements. Abbreviations: TRP, L-tryptophan; KYN, L-kynurenine; 3-HK, 3-DL-hydroxykynurenine; KA, kynurenic acid; ANA, anthranilic acid; 3-HAA, 3-hydroxyanthranilic acid; QA, quinolinic acid; NA, nicotinic acid; XA, xanthurenic acid; and ASC, ascorbic acid.

DETAILED DESCRIPTION OF THE PREFERRED EMBODIMENTS

Definitions

Figure 1:
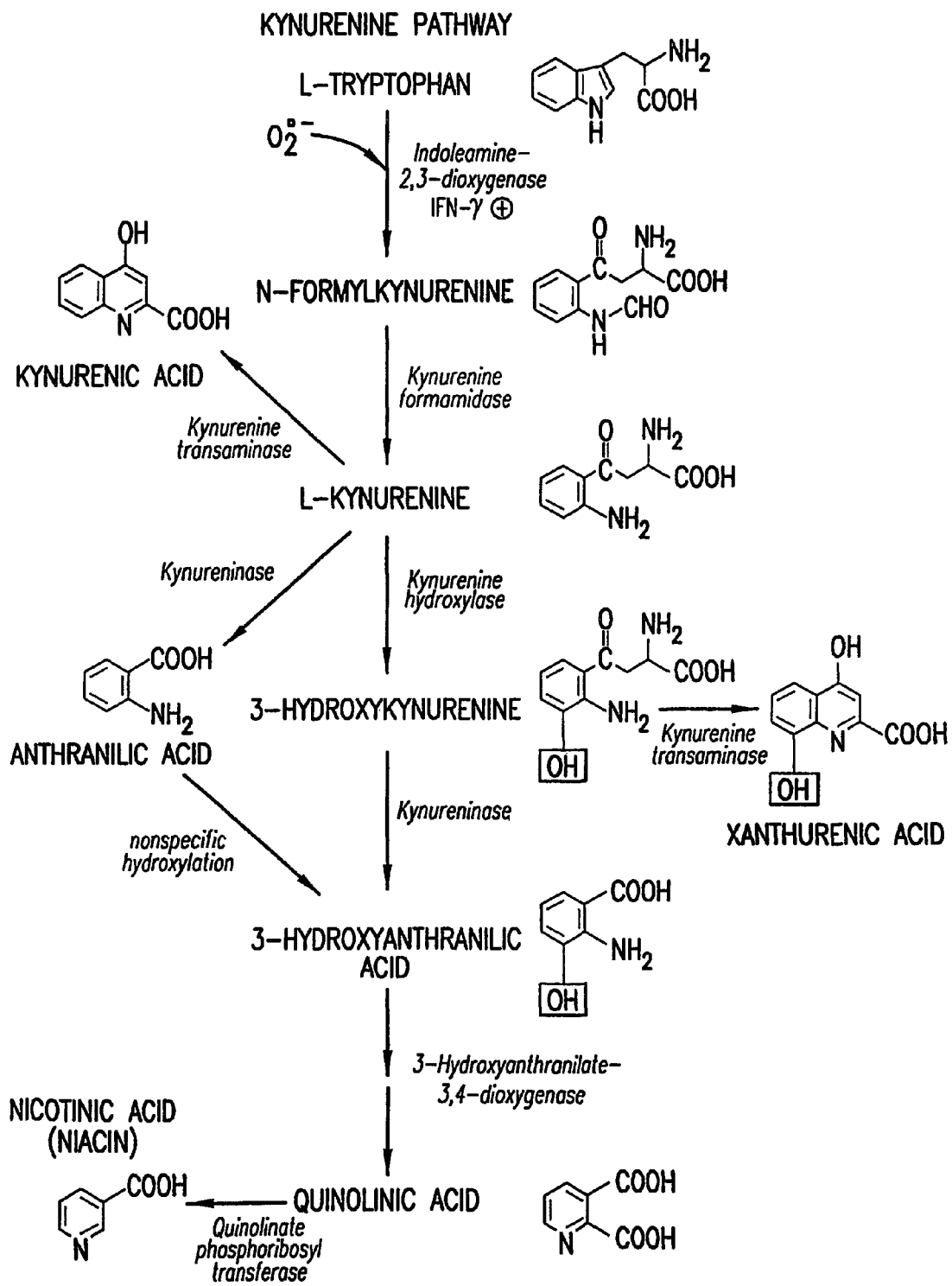
FIG. 1 is a schematic representation of the kynurenine pathway. Enzyme catalyzing reactions are in italics. The rate-limiting reaction is catalyzed by indoleamine-2,3-dioxygenase, which requires the presence of superoxide and is upregulated by interferon gamma. The phenolic hydroxyl group is noted by a box on the compounds that reduce Cu(II) to Cu(I) and generate hydrogen peroxide.

In the description that follows, a number of terms are utilized extensively. In order to provide a clear and consistent understanding of the specification and claims, including the scope to be given such terms, the following definitions are provided.

Chelator: metal-binding molecule characterized by two or more polar groups which participate in forming a complex with a metal ion, and which are generally well-known in the art for the ability to bind metals competitively; and large and small molecules capable of binding metals specifically or non-specifically, such as certain antibiotics.

α-Crystallin Protein: lens protein monomers of approximate monomeric molecular weight 20,000 daltons; purified crystallins. The α-crystallin lens proteins are composed of two subspecies, $\alpha_A$ (aa: 173; MW 19,909 d) and $\alpha_B$ (aa: 175: MW 20,159 d), in a molar ratio which is variable among species (Augusteyn, R. C., and Koretz, J. F., *FEBS Lett.* 222: 1–5 (1987)). These proteins exhibit chaperone and protein surfactant functions (Horwitz, J., *Proc. Natl. Acad. Sci. USA* 89: 10449–10453 (1992); Carver, J. A. et al., *Biochim. Biophys. Acta.* 1204: 195–206 (1994)). $\alpha_A$-Crystallin is found predominantly in the ocular lens, whereas $\alpha_B$-crystallin is also found in extralenticular tissues including heart, muscle and brain (Bhat, S. P. et al., *Eur. J. Biochem.* 202: 775–781 (1991)) and shares homology with and functions as a heat-shock protein (Groenen, P. J. et al., *Eur. J. Biochem.* 225: 1–19 (1994)).

Complexing Agents: molecules with characteristic spectrophotometric spectra when used as indicators of $Cu^+$ or $Fe^{2+}$. By binding to their respective ions specifically and then exhibiting a well known absorption at a known specific wavelength, the measurement of the complexing agents complexed with their ions provides an easy way to quantitate reduced copper and iron ion formation. Bathocuproinedisulfonic acid (BC) anion for $Cu^+$ and bathophenanthrolinedisulfonic acid (BP) anion for $Fe^{2+}$ are the preferred complexing agents for measuring the presence of copper and iron ions, respectively.

The Kynurenine Pathway

A diverse set of findings implicates tryptophan metabolites generated through the kynurenine pathway in a variety of pathological functions. For example, activation of the kynurenine pathway is observed in disorders such as Huntington's Disease (Reynolds, G. B., and Pearson, S. J., *Lancet* 2:979–980 (1989); Pearson, S. J. et al., *Neurosci. Lett.* 144: 199–201 (1992)), Parkinson's Disease (Ogawa, T. et al., *Neurology* 42:1702–1706 (1992)), HIV encephalopathy (Sarder, A. M. et al., *J. Neurochem.* 64:932–935 (1995)), cerebral malaria (Sanni, L. A. et al., *Am. J. Pathol.* 152: 611–619 (1998)), animal models of multiple sclerosis (Flanagan, E. M. et al., *J. Neurochem.* 64:1192–1196 (1995)), fetomaternal tolerance (Munn, D. et al., *Science* 281: 1191–1193 (1998)), poliomyelitis (Heyes, M. P. et al., *Brain* 116: 1425–1450 (1993); Heyes, M. P. et al., *Faseb. J.* 6: 2977–2989 (1992)), and viral pneumonia (Yoshida, R. et al., *Proc. Natl. Acad. Sci. USA* 93: 12553–12558 (1996)).

Two of the kynurenine pathway metabolites, the orthoaminophenol compounds 3-hydroxykynurenine (3-HK) and 3-hydroxyanthranilic acid (3-HAA), are neurotoxic with apoptotic features in primary neuronal cultures (Okuda, S. et al., *Proc. Natl. Acad. Sci. USA* 93:12553–12558 (1996); Okuda S. et al., *J. Neurochem.* 70: 299–307 (1998)).

Kynurenine pathway metabolites and their o-β-D glucoside derivatives are found in the ocular lens (and the retina), wherein the kynurenine pathway is constitutively active in the anterior cortical epithelial cells (Van Heyningen, R., *Exp. Eye Res.* 15: 121–126 (1973); Hood, B. D. et al., *J. of Biol. Chem.* 274: 32547–32550 (1999); Chiarugi, A. et al, *FEBS Lett.* 453:197–200 (1999); Wood, A. M. et al., *Exp. Eye Res.* 56: 317–325 (1993); Bando, M. et al., *J. Biochem. (Tokyo)* 89: 103–109 (1981); Starkebaum, G. and Harlan, J. M., *J. Clin. Invest.* 77: 1370–1376 (1986)). Specifically, 3-HK and its oxidation products interact with lysyl residues of the lenticular crystallin proteins (Stutchbury, G. M., and Truscott, R. J. W., *Exp. Eye Res.* 10:7–13 (1993)). As a natural constituent of the lens, 3-HK may function as an ocular shortwave ultraviolet light filter absorbing maximally at 365 nm (van Heyningen, R., *Nature* 230:393–394 (1971); Wood, A. M. and Truscott, R. J., *Vision Res.* 34: 1369–1374 (1994)). It is present in primate lenses at a concentration of approximately five μM (Chiarugi, A. et al., *FEBS Lett.* 453: 197–200 (1999); Wood, A. M. et al., *Exp. Eye Res.* 56: 317–325 (1993); Bando, M. et al., *J. Biochem. (Tokyo)* 89: 103–109 (1981)). However, a recent study demonstrated that the amount of 3-HK glucoside bound to the lenticular proteins increases with age (Aquilina, J. A. et al., *Biochem.* 38: 11455–11464 (1999)).

3-HK produced in the lenticular epithelium diffuses through the metabolically inactive body of the lens and ultimately effluxes in the vitreous humor. In addition, 3-HK has been shown to foster formation of protein aggregates which may contribute to the brunescent color of cataractous lenses Stutchbury, G. M., and Truscott, R. J., *Exp. Eye Res.* 57:149–155 (1993)) and may play a prominent role in the formation of high molecular weight polymerized aggregates of the crystallin proteins during cataractogenesis.

The interactions of the kynurenine pathway metabolites with redox-active metals and α-crystallin in an in vitro model of cataract formation has been examined. As discussed in the Examples, the o-aminophenol metabolites 3-HK, 3-HAA and XA (but not quinolinic acid and the non-phenolic kynurenine catabolites kynurenine and anthraniclic acid) were shown to powerfully reduce redox-active metals and to generate reactive oxygen species (especially hydrogen peroxide) in the dark and under UV irradiation. Generation of these reactive oxygen species was shown to be metal-dependent, except 3-HK did not generate superoxide in a copper-dependent manner unlike 3-HAA. Furthermore, both 3-HK and 3-HAA potentiated Cu(II)-dependent cross-linking of $\alpha_B$-crystallin.

Upon exploring the interactions between α-crystallin, 3-HK, Cu(II), and Fe(III), it was discovered that 3-HK powerfully reduces Cu(II) to Cu(I). 3-HK does not reduce Fe(III). α-Crystallin, however, after being modified in the dark with 3-HK or 3-HAA, gained enhanced capacity to reduce Cu(II) and Fe(I), and generate hydrogen peroxide. α-Crystallin modified by ascorbate did not share this property. Similarly, exposure of α-crystallin to kynurenine, 3-HK and 3-HAA in the presence of longwave ultraviolet illumination resulted in dramatically enhanced capacity of the altered protein to reduce metal and generate hydrogen peroxide. Again, α-crystallin modified by ascorbate did not share this property.

After reducing Cu(II) to Cu(II), 3-HK recruits oxygen to form $H_2O_2$, $O_2$ and OH=. 3-HK forms covalent adducts on α-crystallin and, after doing so, confers the enhanced Cu-mediated ROS-generating properties to this protein. The postulated transient radicalization of α-crystallin results in readily observable cross-linking, SDS-resistant aggregation, and fragmentation of the protein (3-HK is found co-aggregated in high concentration with α-crystallin in the cataractous lens). This reaction is strongly potentiated by metal chelation and ultraviolet light, a major risk factor for cataract formation. This reaction series, which was not previously known, is likely to be involved in cataract formation.

The data generated from the Examples demonstrate that 3-HK and 3-HAA both react with Cu(II) and molecular oxygen to produce hydrogen peroxide, but only 3-HK can generate hydrogen peroxide by multiple electron transfer from Cu(II) without producing a superoxide intermediate. Similarly, in Alzheimer's disease, the Aβ peptide carries out a two-electron transfer from Cu(II) to molecular oxygen to produce hydrogen peroxide. Since both 3-HK and 3-HAA generate approximately 3-fold more hydrogen peroxide than available Cu(II), the copper is likely cycling between oxidized and reduced states, permitting multiple electron transfers.

The data from the Examples further indicate that in the presence of substoichiometric amounts of Cu(II), 3-HK and 3-HAA simultaneously generate reduced redox-active metal ions and hydrogen peroxide, products that when combined could result in formation of the highly reactive hydroxyl radical by Fenton-type chemistry. However, evidence of hydroxy radical formation using the thiobarbituric acid-reactive substance (TBARS) assay was unattainable. Similarly, evidence of suppression of 3-HK- and 3-HAA-induced $\alpha_B$-crystallin cross-linking with hydroxyl radical scavengers such as dimethyl sulfoxide, salicylate or mannitol was unattainable. Evidence was also unattainable for the suppression of $\alpha_B$-crystallin cross-linking by decreasing hydrogen peroxide levels with catalase. Although these findings do not support a role for the hydroxyl radical in the aggregation of $\alpha_B$-crystallin, the possibility of hydroxyl radical generation cannot be conclusively excluded because this highly reactive species may elude detection in the assays used in the Examples. For example, 3-HK and 3-HAA may promote hydroxyl radical formation by Fenton chemistry and simultaneously serve as sites for hydroxyl radical attack (i.e., act as a hydroxyl radical scavenger) which is consistent with reports that 3-HK has antioxidant properties (Luthra, M., and Balasubramanian, D., *Exp. Eye Res.* 55: 641–643 (1992); Christen, S. et al., *PNAS USA* 87: 2506–2510 (1990); Goshima, N. et al., *Biochem. Biophys. Res. Comm.* 139: 666–672 (1986)). Other investigators have observed generation of the hydroxyl radical in ESR spin-trapping studies of 3-HK and 3-HAA in the presence of $FeCl_3$ and superoxide dismutase (Kuznezova, L. E., *Nature* 222: 484–485 (1969)). A similar mechanism invoking hydroxyl radical generation has been postulated for 3-HK- and 3-HAA-induced damage to DNA, chromatid breakage and translocation (Hiraku, Y. et al., *Carcinogenesis* 16: 349–356 (1995)). The reactivity of these vicinal aminohydroxy compounds with redox-active transition metal ions may be analogous to the redox cycling chemistry observed in vicinal dihyroxy compounds such as dopamine and related catecholamines (Bindoli, A. et al., *Free Radic. Biol. Med.* 13: 391–405 (1992); Levay, G. et al., *Exp. Neurol.* 146 570–574 (1997)).

Thus, the invention takes advantage of our recent in vitro discovery that several metabolites in the kynurenine pathway reduce redox-active metals and foster metal-dependent polymerization and degradation of the crystallin lens proteins. The redox-active 3-HK and 3-HAA may be co-factors in the oxidative damage of proteins, such as α-crystallin, through interactions with redox-active metals. The mechanism for the o-aminophenol effects is likely to involve equilibrium formation of anilino or phenyoxyl radicals with subsequent decay through oxidation to a quinonimine structure (Aquilina, J. A. et al., *Biochem.* 38: 11455–11464 (1999)) by disproportionation, or through dimerization and/or condensation. The observed increased redox activity of the o-aminophenol metabolites 3-HK and 3-HAA compared to their corresponding non-phenolic precursors may be due to resonance stabilization of the o-aminophenol derived radicals. Alternatively, in the proteinaceous environment of the lens, the radicalized o-aminophenol metabolites could react with local proteins (e.g., α-crystallin) leading to protein radicalization, adduct formation, cross-linking and fragmentation.

As noted above, in cataracts, the long-lived lenticular crystallin proteins accumulate post-translational chemical modifications and form high molecular weight cross-linked protein aggregates within the cytosol. The inventive screening assay involves adding test agents to an in vitro incubation system and monitoring the protein cross-linking and disorganization by a variety of methods. An agent capable of attenuating or blocking the protein cross-linking and disorganization may be considered a candidate agent for the prevention or cure of cataracts. Chelators of redox-active transition metals present one such category of agents.

Methods for Identifying Agents Useful in the Prevention and Treatment of Cataracts and for Evaluating Agents as Potential Causes of Cataracts In one aspect, the present invention incorporates the discoveries above to provide an in vitro system for the rapid screening of agents which interfere with the reactions that result in the functional alteration of ocular proteins (e.g., lenticular crystallins) which may lead to cataract formation. The system involves in vitro incubation utilizing: 1) a reducible, redox-active metal source (e.g., aqueous soluble cupric or ferric compounds); 2) one or a combination of the kynurenine metabolites shown to strongly reduce redox-active metals (e.g., 3-HK, 3-HAA, XA or any of the auto-oxidative products of these compounds) and which are known to interact with proteins; 3) a target protein (e.g., α-crystallin); and 4) a test agent or agents. The intensity of the reaction may be modified by varying the degree of UV irradiation and the oxygen tension. Protein cross-linking, the structural change characteristic of cataract formation (and/or generation of reactive oxygen species), is utilized as the assay endpoint.

The cross-linking of, for example, α-crystallin by 3-HK or 3-HAA and copper is easily monitored by, e.g., Western blot. Accordingly, one aspect of the invention is a screening assay, adaptable for high-throughput, for the evaluation of candidate agents which interfere with the above-described pathway and are therefore useful in the prevention or treatment of cataracts. A variety of methods may be utilized for endpoint measurement, including Western blotting, filtration assays, aggregation/sedimentation methods, turbidometry, fluorometry, spectrophotometry, lens or retinal culture combined with light microscopy or light scattering technology. An agent capable of attenuating or blocking the protein cross-linking is considered to be a candidate for the prevention or treatment of cataracts. The agent to be evaluated in the assay may be a potential drug for treating cataract patients, or those who may be in danger of developing cataracts.

Accordingly one aspect of the invention relates to a method for the identification of an agent to be used in the treatment or prevention of cataracts, wherein the agent decreases or prevents cross-linking of a target protein, comprising:

(a) adding a reducible redox-active metal source to a first target protein sample comprising an auto-oxidizing kynurenine pathway metabolite;

(b) allowing the first target protein sample to incubate for an amount of time sufficient to allow cross-linking of the target protein;

(c) adding the reducible redox-active metal source to a second target protein sample comprising an auto-oxidizing kynurenine pathway metabolite, the second sample additionally comprising a candidate pharmacological agent;

(d) allowing the second sample to incubate for the same amount of time as the first sample;

(e) determining the amount of target protein cross-linking by the first sample and the second sample; and (f) comparing the amount of target protein cross-linking produced by the first sample to the amount of target protein cross-linking produced by the second sample;

whereby a decrease in the amount of target protein cross-linking produced by the second sample, as compared to the first sample, indicates that the candidate pharmacological agent is useful in the treatment or prevention of cataracts.

In a preferred embodiment, the target protein is α-crystallin.

In another preferred embodiment, the reducible redox-active metal source comprises Fe(III). Most preferably, the reducible redox-active metal source comprises Cu(II). These metal ions may be used in combination with small coordinating molecules such as amino acids and other metal coordinating molecules.

In a preferred embodiment, the auto-oxidizing kynurenine pathway metabolite is an o-aminophenol compound. More preferably, the o-aminophenol compound is selected from the group consisting of 3-hydroxykynurenine, 3-hydroxyanthranilic acid, and xanthurenic acid. Still more preferably, the o-aminophenol compound is 3-hydroxyanthranilic acid. Most preferably, the o-aminophenol compound is 3-hydroxykynurenine.

In another preferred embodiment, two or more different test candidate agents are simultaneously evaluated for an ability to alter target protein cross-linking.

In another preferred embodiment, the first and second target protein samples are incubated under ultraviolet B irradiation.

In another preferred embodiment, the amount of cross-linked target protein in the first and second sample is determined by a method selected from the group consisting of Western blotting, filtration assay, aggregation/sedimentation, turbidometry, fluorometry, spectrophotometry, and lens or retinal culture combined with light microscopy or light scattering technology.

In a preferred embodiment of the invention, redox-active metals are present at a final concentration of about 1–25 µM, preferably about 25 µM. The test agent to be screened is present at a final concentration ranging from about 10–200 µM, preferably about 50 µM. Kynurenine pathway metabolites are present at a final concentration of about 1–25 µM, preferably about 10 µM. A non-hydroxylated metabolite at the same concentration may be substituted as a negative control. The lens protein may be recombinant or purified crystallins (about 10–50 µg/ml). Total lens protein may be at a final concentration of about 50–500 µg/ml.

In another embodiment of the invention, using the same assay detecting the degree of target protein cross-linking, agents used or to be used in the treatment of humans or animals, released into the environment, or used industrially may be screened and evaluated. Detection of agents that potentiate, cause or accelerate cataracts allows measures to be taken to reduce or eliminate human or animal contact with such agents, thereby reducing the number and severity of cataracts still formed. Thus, the assay may be used to evaluate agents as a potential cause, accelerator or potentiator of cataract formation, wherein the agent increases or accelerates cross-linking of a target protein, comprising:

(a) adding a reducible redox-active metal source to a first target protein sample comprising an auto-oxidizing kynurenine pathway metabolite;

(b) allowing the first target protein sample to incubate for an amount of time sufficient to allow cross-linking of the target protein;

(c) adding the reducible redox-active metal source to a second target protein sample comprising an auto-oxidizing kynurenine pathway metabolite, the second sample additionally comprising a candidate agent to be evaluated;

(d) allowing the second sample to incubate for the same amount of time as the first sample;

(e) determining the amount of target protein cross-linking by the first sample and the second sample; and (f) comparing the amount of target protein cross-linking produced by the first sample to the amount of target protein cross-linking produced by the second sample;

whereby an increase in the amount of target protein cross-linking produced by the second sample as compared to the first sample indicates that the candidate agent being tested may potentiate or accelerate the formation of cataracts.

In a preferred embodiment, the target protein is α-crystallin.

In a preferred embodiment, the reducible redox-active metal source comprises Fe(III). Most preferably, the reducible redox-active metal source comprises Cu(II). These metal ions may be used in combination with small coordinating molecules such as amino acids and other metal coordinating molecules.

In a preferred embodiment, the auto-oxidizing kynurenine pathway metabolite is an o-aminophenol compound. More preferably, the o-aminophenol compound is selected from the group consisting of 3-hydroxykynurenine, 3-hydroxyanthranilic acid, and xanthurenic acid. Still more preferably, the o-aminophenol compound is 3-hydroxyanthranilic acid. Most preferably, the o-aminophenol compound is 3-hydroxykynurenine.

In another preferred embodiment, two or more different test candidate agents are simultaneously evaluated for an ability to alter target protein cross-linking.

In another preferred embodiment, the first and second target protein samples are incubated under ultraviolet B irradiation.

In another preferred embodiment, the amount of cross-linked target protein in the first and second sample is determined by a method selected from the group consisting of Western blotting, filtration assay, aggregation/sedimentation, turbidometry, fluorometry, spectrophotometry, and lens or retinal culture combined with light microscopy or light scattering technology.

In a preferred embodiment of the invention, redox-active metals are present at a final concentration of about 1–25 µM, preferably about 25 µM. The test agent to be screened is present at a final concentration ranging from about 10–200 µM, preferably about 50 µM. Kynurenine pathway metabolites are present at a final concentration of about 1–25 µM, preferably about 10 µM. A non-hydroxylated metabolite at the same concentration may be substituted as a negative control. The lens protein may be recombinant or purified crystallins (about 10–50 µg/ml). Total lens protein may be at a final concentration of about 50–500 µg/ml.

Complexing Agents

In an alternative embodiment, the Cu(I) produced by a protein sample is complexed with a complexing agent having an optimal visible absorption wavelength. The amount of Cu(I) produced by the sample is then detected using optical spectrophotometry or fluorometry (see Examples 1 and 2). By specifically binding to their respective ions and then exhibiting a well known absorption at a known specific wavelength, the measurement of the complexing agents complexed with their reduced ions provides an easy way to quantitate reduced copper and iron ion formation. Example 1 discusses the theory behind such spectral analysis. In a preferred embodiment, the complexing agent to be used for the determination of the amount of $Cu^+$ produced is bathocuproinedisulfonic acid anion (BC) (see Example 2). The complex $Cu^+$—BC has an optimal visible absorption wavelength of about 483 nm. 3-HK, 3-HAA or XA will produce $H_2O_2$ and $Cu^+$ almost immediately following the addition of Cu(II) to the reaction mixture. Thus, BC may be added to the reaction immediately following the addition of Cu(I) to the 3-HK, 3-HAA or XA samples. The concentration of BC to be achieved in a sample is between about 10 µM to about 400 µM, more preferably about 75 µM to about 300 µM, and still more preferably about 150 µM to about 275 µM. In the most preferred embodiment, the concentration of BC to be achieved in a sample is about 200 µM. Of course, one of ordinary skill in the art can easily optimize the concentration of BC to be added with no more than routine experimentation. Other complexing agents such as bicinchoninic acid could be used in a similar manner.

Wherein the amount of Fe(II) produced is to be determined, the complexing agent to be used is, for example, bathophenanthrolinedisulfonic acid (BP) anion (see Examples 1 and 2). The complex $Fe^{2+}$—BP has an optimal visible absorption wavelength of about 535 nm. 3-HK will produce $H_2O_2$ and Fe(II) almost immediately following the addition of Fe(III) to the reaction mixture. Thus, BP may be added to the reaction immediately following the addition of Fe(III) to the 3-HK samples. The concentration of BP to be achieved in a sample is between about 10 µM to about 400 µM, more preferably about 75 µM to about 300 µM, and still more preferably about 150 µM to about 275 µM. In the most preferred embodiment, the concentration of BP to be achieved in a sample is about 200 µM. The concentration of BP to be added can be easily optimized with no more than routine experimentation. For example, to a known concentration of metal ions, increasing amounts of complexing agent, such as BP, are added and absorption spectral readings taken. When the addition of BP no longer results in increasing spectral measurements at the characteristic wavelength, then all the available reduced metal ions are complexed. Generally, it is good to have a slight excess of complexing agent.

Treatment of Cataracts

In another embodiment of the invention, the assay method of the present invention may be used to evaluate redox-active transition metal chelators suitability as pharmaceutical agents useful in preventing or treating an injury to or disease of the ocular lens, retina and/or macula, such as age-related cataracts in a mammal. Thus, in another embodiment, the invention relates to a method of treating or preventing injuries to or diseases of the ocular lens, retina and/or macula comprising administering to a mammal in need thereof a chelator-containing pharmaceutical composition.

The causes of such injury include, but are not limited to, trauma to the retina, lens and/or macula, surgery, chemicals, photic or other electromagnetic radiation, etc. Ocular diseases include, but are not limited to, aging and degeneration, progression of a comorbid condition, age-related cataracts, macular degeneration, oxygen-induced retinopathy, inflammatory conditions, infections, etc.

The interaction of 3-HK and 3-HAA with redox-active metal ions and proteins may occur in a variety of biochemical settings. During conditions of local acidosis, such as inflammation or infection, copper and iron are liberated from proteins and thus, are made available for redox reactions and protein interactions (Halliwell, B. et al., *Philos. Trans. R. Soc. Lond. B. Biol. Sci.* 311: 659–671 (1985); Halliwell, B., and Gutteridge, J. M., *Biochem. J.* 219 1–14 (1984); Gutteridge, J. M., *Biochem. J.* 245: 415–421 (1987)). These conditions also activate cells of the macrophage/monocyte lineage. For example, indoleamine-2,3-dioxygenase, the rate-limiting enzyme in the kynurenine metabolic pathway, is induced by interferon-γ (Yoshida, R. et al., *PNAS USA* 76: 4084–4086 (1979); Taylor, M. W., and Feng, G. S., *Faseb. J.* 5: 2516–2522 (1991)), a factor release during inflammation and infection. This enzyme consumes the superoxide anion generated during the macrophage respiratory burst for activity. The net result of these reactions is increased production of the kynurenine pathway metabolites, including 3-HK and 3-HAA, and the generation of ROS.

The reduction of copper and iron by 3-HK and 3-HAA and the generation of ROS and subsequent protein damage may serve a physiological function during infection by damaging proteins or infectious agents and facilitating their functional inactivation, degradation and clearance. However, inappropriate activation of this pathway may contribute to degenerative or inflammatory conditions by facilitating oxidative damage to important host proteins. The redox-active transition metal chelator may then be administered to a mammal in a therapeutically effective amount to interfere with the reactions that result in the functional alteration of proteins such as the lenticular crystallins.

The preferred redox-active transition metal chelator is selected from the group consisting of bathocuproine, bathophenanthroline, triethylenetetramine, diethylenetriaminepentaacetic acid, penicillamine, clioquinol, desferroxamine, and derivatives, homologues, analogues, prodrugs or pharmaceutically acceptable salts or esters thereof. Among the most preferred redox-active transition metal chelators are hydrophobic, i.e., lipophilic, chelators that can cross the plasma membrane and permeate the cytosol, such as clioquinol or a derivative, homologue, analogue, prodrug or pharmaceutically acceptable salt or ester thereof. The most preferred metal chelator is clioquinol. Clioquinol is a chelating agent that may be administered at between about 1.0–30 mg/kg body weight of the patient in two to three divided doses per day, and more preferably, about 5–20 mg/kg.

The chelator to be administered may be in the form of a substantially purified extract from a plant, wherein the chelator is extracted using an organic solvent.

A therapeutically effective amount of the redox-active chelator administered encompasses an amount effective to slow the destruction or degeneration of the ocular lens, retina and/or macula caused by a disease; promote eye function and survival after injury; improve the recovery of or ameliorate visual deficits in a mammal that has sustained damage to the ocular lens, retina and/or macula as a result of a loss of lens, retina and/or macula function; reduce the rate of impairment that occurs over time as the ocular lens, retina and/or macular injury or disease progresses; and/or protect the lens, retina and/or macula from damage or death due to exposure to toxic agents.

The chelator is administered intracerebrally, intraperitoneally, intramuscularly, intraventricularly, intravenously by injection, orally, topically, sublingually, bucally, vaginally, rectally, parenterally or intraocularly. As would be understood by one of ordinary skill in the art, when the chelator is administered to an individual, it may be in a composition which contains salts, buffers, adjuvants, or other substances which are desirable for improving the efficacy of the composition. Examples of materials suitable for use in preparing pharmaceutical compositions are provided in numerous sources including *Remington's Pharmaceutical Sciences*, Osol, A., ed., 18th Edition, 1990, Mack Publishing Co., Easton, Pa.

For parenteral administration, preparations containing the chelator drug may be provided to a patient in need of such treatment in combination with pharmaceutically acceptable sterile aqueous solvents, e.g., physiological saline, or non-aqueous solvents, suspensions and emulsions. Examples of non-aqueous solvents are propylene glycol, polyethylene glycol, vegetable oils such as olive oil, and injectable organic esters such as ethyl oleate. Aqueous carriers include water, water-alcohol solutions, Ringer's dextrose solution, dextrose plus sodium chloride solution, Ringer's solution containing lactose, and fixed oils.

For injectable use, sterile aqueous solutions (where water soluble) are generally used or alternatively sterile powders for the extemporaneous preparation of sterile injectable solutions may be used. The pharmaceutical compositions must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. Preventing the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

When the chelator is suitably protected, it may be orally administered, for example, with an inert diluent or with an assimilable edible carrier, or they may be enclosed in hard or soft shell gelatin capsule, compressed into tablets, or incorporated directly with food in the diet. For oral therapeutic administration, the chelator may be incorporated with excipients and used in the form of ingestible tablets, buccal tablets, troches, capsules, elixirs, suspensions, syrups, wafers, and the like. Such compositions and preparations should contain at least about 1% by weight of active compound. The percentage of the compositions and preparations may, of course, be varied and may conveniently be between about 5 to about 80% of the weight of the unit.

The tablets, troches, pills, capsules and the like may also contain other components such as listed hereafter: a binder such as gum, acacia, corn starch or gelatin; an excipient such as dicalcium phosphate; a disintegrating agent such as corn starch, potato starch, alginic acid and the like; a lubricant such as magnesium stearate; a sweetening agent such a sucrose, lactose or saccharin may be added; and/or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the chelator, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the chelator may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the chelator, use thereof in the therapeutic compositions is contemplated.

The chelator may be administered after an injury has occurred, after a disease has been discovered, before an expected injury or before the occurrence of a disease which is expected to occur.

The following examples are provided by way of illustration to further describe certain preferred embodiments of the invention, and are not intended to be limiting of the present invention, unless specified.

EXAMPLES

Materials—Metal ion standard solutions (10 mg/ml in 10% $HNO_3$) were purchased from the National Institute of Standards and Technology, Gaithersburg, Md; The hydrogen peroxide indicator 2',7'-dichlorofluorescein diacetate was purchased from Molecular Probes, Eugene, Oreg. Total lens protein was freshly prepared from a calf eye obtained from a local abbatoir. Recombinant human $\alpha_B$-crystallin was the generous gift of Dr. J. Liang, Brigham and Women's Hospital, Boston, Mass. (Sun, T. X. et al., *J. Biol. Chem.* 272: 6220–6225 (1997)). Polyclonal rabbit antibodies directed against either $\alpha_A$-crystallin or $\alpha_B$-crystallin were the generous gift of Dr. J. Horwitz, University of California, Los Angeles. All other reagents were purchased from Sigma, St. Louis, Mo. unless otherwise noted. All solutions were prepared in filtered sterilized CHELEX™-treated (CHELEX™ 100 chelating ion exchange resin, Bio-Rad, Hercules, Calif.) Dulbecco's phosphate buffered saline without calcium or magnesium (PBS: KCl 2.7 mM, $KH_2PO_4$ 1.4 mM, NaCl 137 mM, $Na_2HPO_4$ 7.68 mM), pH adjusted to 7.4. Cu(II)-Gly and Fe(III)-citrate stock solutions were used to prevent metal-hydroxy and metal-oxy polymers that form in neutral metal ion solutions. Working stock solutions of Cu(II)-glycine or Fe(III)-citrate metal ions were prepared in PBS, pH 7.4, by dilution of the standard metal ion stocks with ligands in a molar ratio of 1:6.

The data demonstrate that o-aminophenol metabolites of kynurenine, but not their respective non-hydroxylated precursors, potently reduce Cu(II)>Fe(III) and subsequently engender Cu- and $O_2$-dependent production of hydrogen peroxide. In the presence of α-crystallin, both 3-HK and 3-HAA promote SDS-resistant polymerization which is also Cu-dependent. Both 3-HK and 3-HAA are also known to directly bind to lens proteins such as crystallins through lysyl residues resulting in aggregation, pigmentation, and development of a distinct blue (non-tryptophan) fluorescence which are all properties characteristic of nuclear cataract formation (Van Heyningen, R., *Exp. Eye Res.* 15: 121–126 (1973); Wood, A. M. and Truscott, R. J., *Exp. Eye Res.* 56: 317–325 (1993); Stutchbury, G. M. and Truscott, R. J., *Exp. Eye Res.* 57: 149–155 (1993); Benavente, M. G. and Truscott, R. J., *Arch. Biochem. Biophys.* 290: 451–457 (1991)). The data show that the SDS-resistant polymerization is redox-metal dependent, and α-crystallin tanned with either 3-HK or 3-HAA has increased ability to reduce redox-active metal, especially Cu(II). Further, it was found that in the presence of total lens protein or purified recombinant $\alpha_B$-crystallin, both 3-HK and 3-HAA promote SDS- and β-mercaptoethanol-resistant cross-linking of $\alpha_B$-crystallin in a Cu-dependent manner.

UV light-induced crystallin cross-linking is enhanced by 3-HK and 3-HAA (Zigler, J. S. Jr. and Goosey, J. D., *Photochem. Photobiol.* 33: 869–874 (1981)). The data, however, indicate that 3-K and 3-HAA foster protein cross-linking even in the dark when Cu(II) is present. Indeed, the presence of redox-active metal ions appears to be a prerequisite condition for the cross-linking reaction since the addition of a chelator suppresses the reaction. In contrast to the effects of 3-HK and 3-HAA on the cross-linking of $\alpha_B$-crystallin, these kynurenine metabolites fostered the depletion of bovine serum albumin and myelin basic protein (Dykens, J. A. et al., *Biochem. Pharmacol.* 36: 211–217 (1987); Truscott, R. J. and Martin, F., *Exp. Eye Res.* 49 927–940 (1989)). The differences in 3-HK- and 3-HAAinduced protein oxidation may reflect the local protein microenvironment in which the o-aminophenol metabolites and Cu(II) react.

Most redox-active metals in biological systems are bound to protein and small biomolecules and are not present as free metal ions. However, two scenarios may be operative in the lens which argue for redox-active metal ion availability. First, protein-bound metal ions can be liberated by acidosis, a condition present in the nucleus of the lens (Mathias, R. T. et al., *J. Gen. Physiol.* 98: 1085–1103 (1991)). Thus, metal ions which may be less tightly bound to nuclear proteins may be more available for reaction with 3-HK and 3-HAA. Second, the proposed reactions may be carried out in the local environment of the protein-bound metal. Therefore, an increase in free redox-active metal ions in the lens may not be obligatory for these reactions to occur. Indeed, protein-bound copper complexes can catalyze some reactions similar to those observed withe free copper (Mathias, R. T., et al., *J. Gen. Physiol.* 98: 1085–1103 (1991); Starkebaum, G. and Harlan, J. M., *J. Clin. Invest.* 77: 1370–1376 (1986)). These mechanisms may not be mutually exclusive.

The present data are consistent with a common redox biochemistry which may contribute to the oxidative damage noted in age-related cataracts. Moreover, the present data suggest that targeted chelation of redox-active metals or displacement with non-redox active metals such as zinc, may have therapeutic potential in preventing or treating age-related cataracts. The redox metal reactions in the present study may also apply to kynurenine metabolites that may attach to other proteins as adducts.

Only tryptophan metabolites possessing an o-aminophenol group (ie., 3-HK and 3-HAA) are redox active. The mechanism for the o-aminophenol effects is likely to involve equilibrium formation of anilino and phenoxyl radicals with subsequent decay through oxidation to a quinonimine structure by disproportionation, or through dimerization and/or condensation. Alternatively, the radicalized o-aminophenol metabolites could react with local proteins (e.g., structural proteins such as α-crystallin within the lens) leading to protein radicalization, adduct formation, cross-linking, and fragmentation. The observed redox activity of the o-aminophenol metabolites 3-HK and 3-HAA relative to their corresponding non-phenolic precursors may be related to resonance stabilization of the proposed o-aminophenol derived radicals.

3-HK and 3-HAA are both known to auto-oxidize. Specifically, 3-HAA auto-oxidizes to produce the red pigment cinnabarinic acid and concomitantly produce superoxide anion and hydrogen peroxide. 3-HK, on the other hand, dimerizes to the brown chromophore xanthommatin in the presence of UV irradiation. The present findings indicate that, in the presence of substoichiometric amounts of Cu(II), 3-HK and 3-HAA simultaneously generate reduced metal and hydrogen peroxide, products that when combined could result in formation of the highly reactive hydroxyl radical by Fenton-type chemistry.

Example 1

Metal Reduction Assays—Assays were performed using a 96-well microtiter plate (Costar, Mass.). Test compounds from the kynurenine pathway (10 μM) or, as a positive control, ascorbic acid (ASC, 10 μM) were co-incubated with either Fe(III)-citrate (25 μM) and the Fe(II) indicator bathophenanthroline disulfonic acid (BP, 250 μM), or Cu(II)-glycine (25 μM) and the Cu(I) indicator bathocuproine disulfonic acid (BC) or bicinchoninic acid (BCA, 250 μM). Incubations were conducted in PBS, pH 7.4, at 37° C. in the dark for one hour. Absorbencies were then measured using a plate reader (SPECTRAmax Plus, Molecular Devices, CA) at the appropriate wavelengths: Fe(II)-BP complex at 535 nm (the known molar absorption coefficient, $M_{535}$,=22140 $M^{-1}cm^{-1}$), Cu(I)-BC complex at 483 nm, $M_{483}$=12250 $M^{-1}cm^{-1}$), or Cu(I)-BCA complex at 562 nm, $M_{562}$=7700 $M^{-1}cm^{-1}$). In control samples, absorbance from the metal ion and indicator in the absence of test compound and the absorbance of test compound in the presence of metal ions, but in the absence of indicator, were determined. The absorbencies from these controls were deducted from those obtained in the presence of the test compound, metal and indicator to yield the net absorbance ($\Delta A$). Fe(II) or Cu(I) concentrations (μM) were calculated according to the formula: $C(\mu M) = \Delta A * 10^6 / M_\lambda$.

Figure 2A:
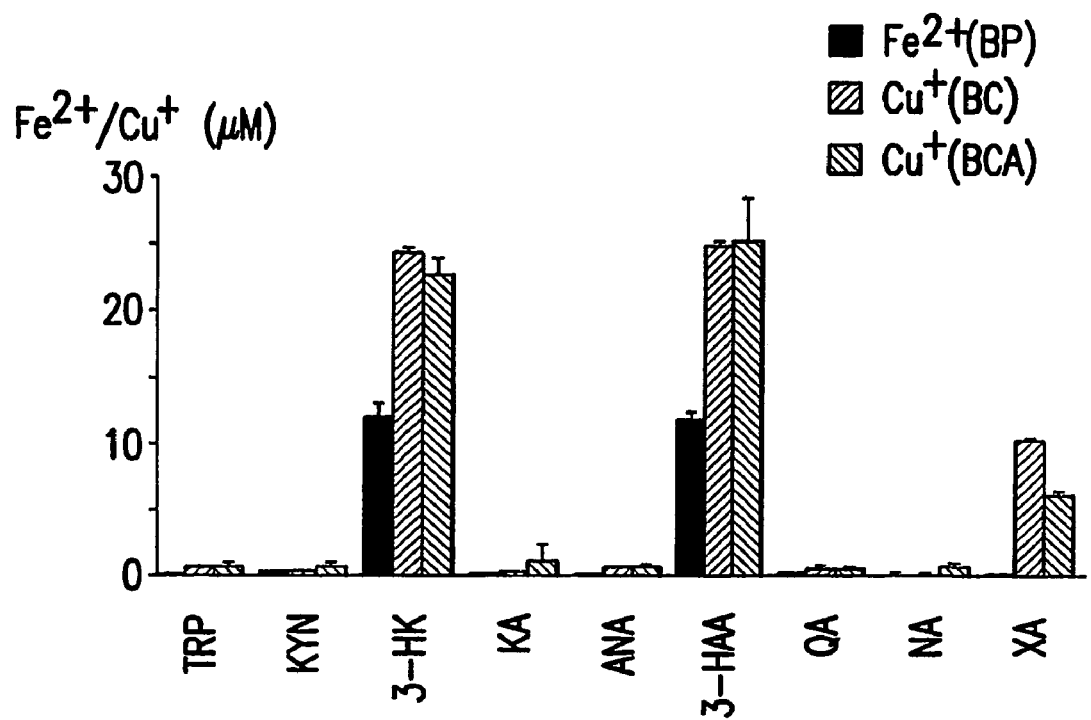
FIGS. 2A and 2B.
Figure 2B:
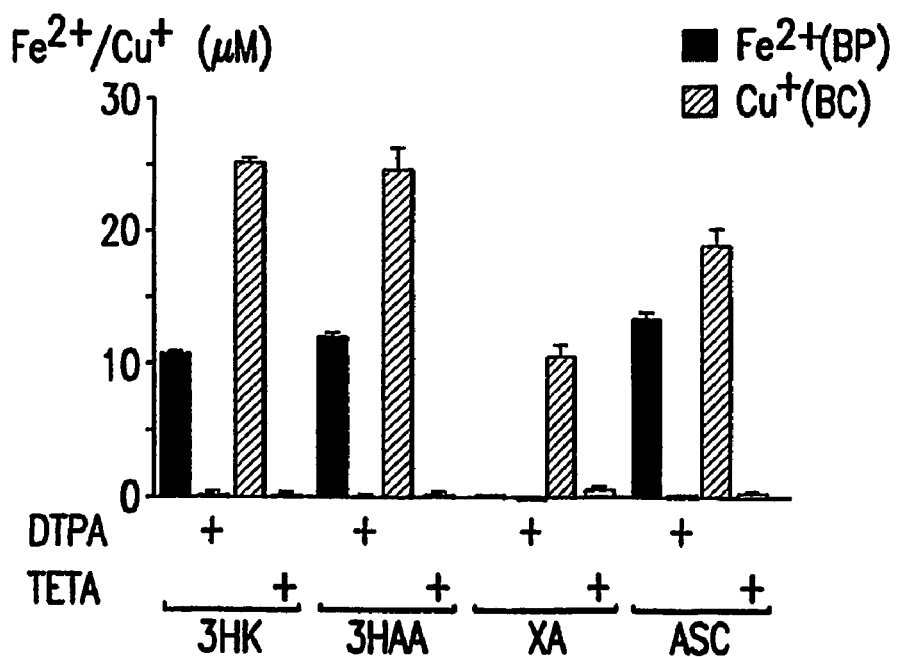
Figure 3A:
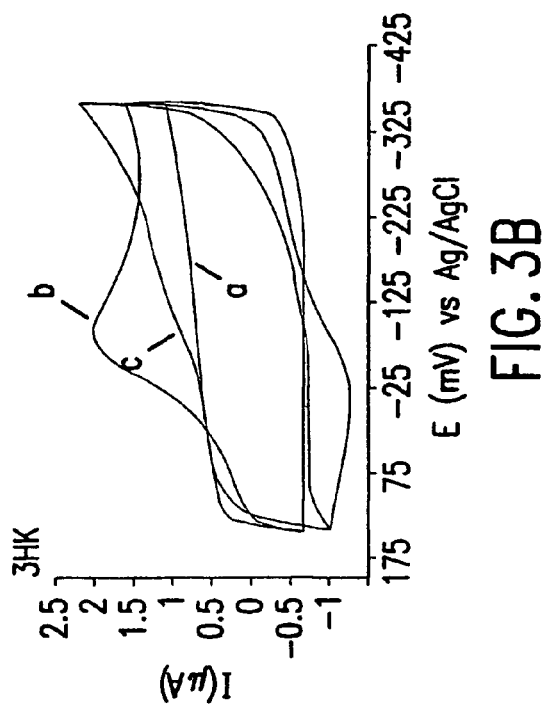
FIGS. 3A–3D are graphs showing electrochemical analysis by cyclic voltammetry of KYN, 3-HK, ANA and 3-HAA (100 µM) in the presence of copper chloride (25 µM). In each panel, voltammograms are shown for (a) background in PBS; (b) Cu(II) in PBS; and (c) Cu(II) in the presence of each of the designated metabolites.
Figure 3B:
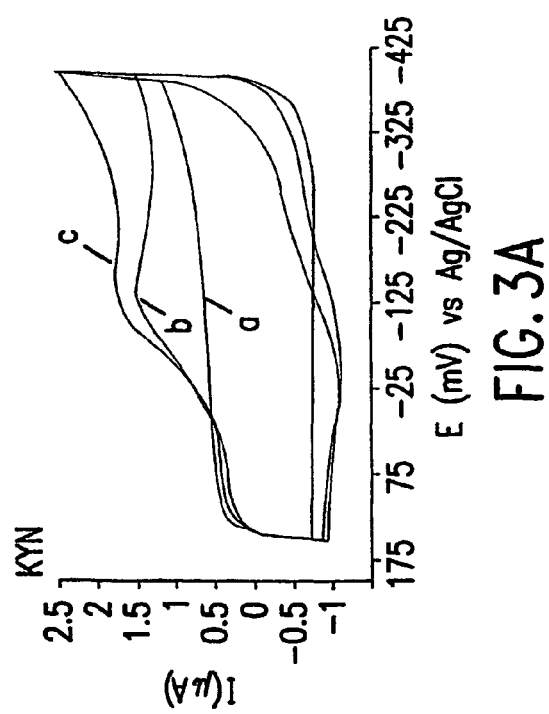
Figure 3C:
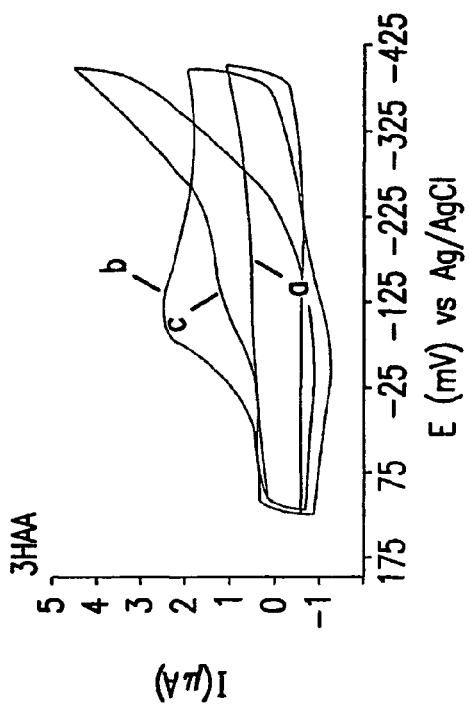
Figure 3D:
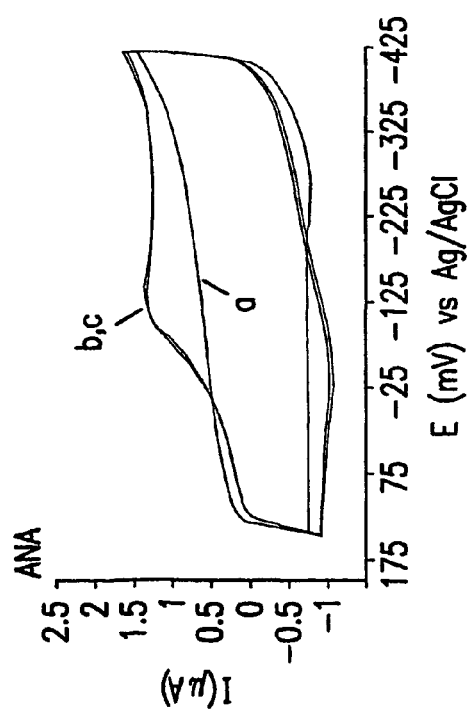

The compounds comprising the kynurenine pathway (FIG. 1) were assayed for their ability to reduce Fe(II) and Cu(II) (FIG. 2A). The ortho-aminophenol kynurenine metabolites, 3-HK and 3-HAA, potently reduced Cu(II) (100%) and Fe(III) (approximately 50%), whereas the dihydroxyquinaldic acid kynurenine metabolite, xanthurenic acid (XA), reduced Cu(II) approximately 40%, but did not reduce Fe(III). The high-affinity metal cationic chelator diethylenetriaminepentaacetic acid (DTPA) (250 μM) and the high-affinity Cu(II) chelator triethylenetetramine (TETA) (250 μM) both abolished metal reduction by 3-HK, 3-HAA and XA (FIG. 2B), indicating that the signal observed was due to metal reduction and not to a nonspecific interaction of the active metabolites with the indicator compounds. The reduction of Fe(III) and Cu(II) by ascorbic acid (ASC), the positive control, was also abolished by chelation. The measurements have been corrected for background absorbency due to the metal ions and indicator compound. Values represent the mean±SD for three independent measurements. 3-HK and 3-HAA, each at 10 μM, were able to reduce 25 μM Cu(II), suggesting that more than one electron is transferred from these tryptophan metabolites to Cu(II). The other kynurenine metabolites (FIG. 2A) were ineffective reducing agents for either Cu(II) or Fe(III). Since BC could potentially increase the oxidation potential of Cu(II) (Sayre, L. M., *Science* 274: 1933–1934 (1996)), the bicinchoninic acid (BCA) assay was employed to corroborate Cu(II) reduction and it was found that the reduction efficiencies of the agents examined were in close agreement with the values determined by the bathocuproine method (FIG. 2A).

Example 2

Cyclic Voltammetry—Cyclic voltammetry was performed at room temperature (22±2° C.) on ambient solutions using an EG&G PAR potentiostat, Model 273. The potentiostat was operated in Ramp Mode, generating a potential staircase waveform with a 0.25 mV step height. The potential window of +0.15 to −0.4V, in which Cu(I) is electroactive, but the metabolites are not, was scanned in both directions at a rate of 100 mV/sec. The current response was passed through a 5.3 Hz low pass filter. A minimum of three cycles were collected for each scan, ensuring the stability of the electrochemical response. The electrochemical cell consisted of an indium/tin oxide working electrode (Delta Technologies) with an active area of 0.32 cm², a platinum wire auxiliary electrode, and a Ag/AgCl (1 M KCl) reference electrode (Microelectrodes Inc.). Both the auxiliary and reference electrodes were positioned in the cell in close proximity to the working electrode. The working electrodes were pretreated with successive 10 minute sonications in Alconox (~8 g/L), 95% ethanol, Milli-Q purified $H_2O$ (2×), and PBS (pH 7.4), followed by an overnight soak in PBS (pH 7.4). The ITO electrodes were subsequently "activated" immediately prior to use by successive cycling in PBS for three cycles in each of the following potential windows: +0.15↔−0.4 V, +0.4↔−0.4 V, and +1.0↔−0.4 V. Cupric chloride (25 µM; Allied Chemical) was used as the Cu(II) source. Background voltammograms were obtained on each new electrode before testing the kynurenine pathway metabolites. PBS solutions of KYN, 3-HK, ANA, and 3-HAA (each at 100 µM) were separately scanned with and without added Cu(II) (25 µM). Each experiment also included a scan of Cu(II) (25 µM) in PBS without added test compound. All solutions were tested within minutes of being prepared. Each test was repeated to ensure the reproducibility of the results. The results are shown in FIGS. 3A–3D.

The voltammograms in FIGS. 3A–3D compare 3-HK and 3-HAA to their corresponding non-phenolic analogs, kynurenine (KYN) and anthranilic acid (ANA), in aqueous solutions of Cu(II) at pH 7.4. Cyclic voltammetry of the four metabolite compounds in the absence of Cu(II) (data not shown) revealed no significant redox activity in the +0.15 to −0.4 V potential window compared to the PBS background (scan "a" in each panel). At potentials above +0.15 V, the metabolites undergo direct irreversible oxidation, a reaction that is not considered further here. Cyclic voltammetry of Cu(II) in PBS yielded a current response at ≈−100 mV due to reduction of the metal ion (scan "b" in each panel). In the presence of either KYN or ANA, the Cu(II) reduction wave was largely unaffected (KYN and ANA panels, scan "c") although KYN appears to show some slight reactivity. This result suggests that most of the Cu(II) remains uncomplexed and available for reduction in the presence of these two metabolites. The Cu(II) reduction wave was nearly abolished in the presence of 3-HK (3-HK panel, scan "c"), and markedly decreased in the presence of 3-HAA (3-HAA panel, scan "c").

These results indicate that removal of electrochemically active Cu(II) occurs by complexation of the copper to the test agent, thus making the copper inaccessible to reduction at the electrode surface. Alternatively or simultaneously, the removal of electrochemically active Cu(II) could occur by reduction of the Cu(II) by the test compound itself so that no further reduction can be detected at the electrode. Either or both occur in the presence of 3-HK and 3-HAA, but not in the presence of kynurenine or anthranilic acid, a finding consistent with the reduction of Cu(II) by these ortho-aminophenol kynurenine pathway metabolites (FIG. 2).

Example 3

Hydrogen Peroxide Assay—The fluorometric assay for hydrogen peroxide is based on the dichlorofluorescein diacetate (DCF) method (Molecular Probes, Eugene, Oreg.). The DCF solution (5 mM) in 100% ethanol was deacetylated in the presence of 0.01 M NaOH for 30 minutes and neutralized. Horseradish peroxidase (200 U/ml) was then added and the DCF concentration adjusted to 200 µM in PBS. The reaction solutions were carried out in PBS, pH 7.4, in a 96-well format plate (total volume=300 µL/well) and contained a test compound (KYN, 3-HK, 3-HAA, ANA, or ASC, each at 10 µM), deacetylated DCF (20 µM), and Cu(II)-glycine (1 µM) as indicated, incubated at 37° C. for 60 minutes. Reactions were conducted in the dark to avoid photodynamic effects. Abolition of the reading by co-incubation with catalase (1000 U/ml) was used for establishing $H_2O_2$ specificity. The fluorescent readings were recorded by a Packard FLURORCOUNT™ fluorescent plate reader with a 485 nm excitation filter and 530 nm emission filter. Concentrations were determined by comparison to a standard curve using reagent grade hydrogen peroxide in CHELEX™ chelating ion exchanae resin-treated PBS buffer, pH 7.4.

Figure 4A:
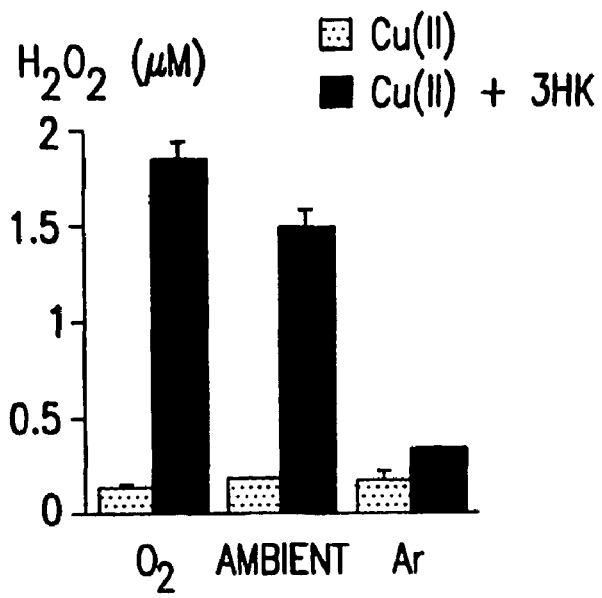
FIGS. 4A–4C are graphic depictions of hydrogen peroxide production in the presence of the aminophenolic kynurenine metabolites, ascorbic acid, TETA and catalase. Values represent the mean±SD for three independent measurements.
Figure 4B:
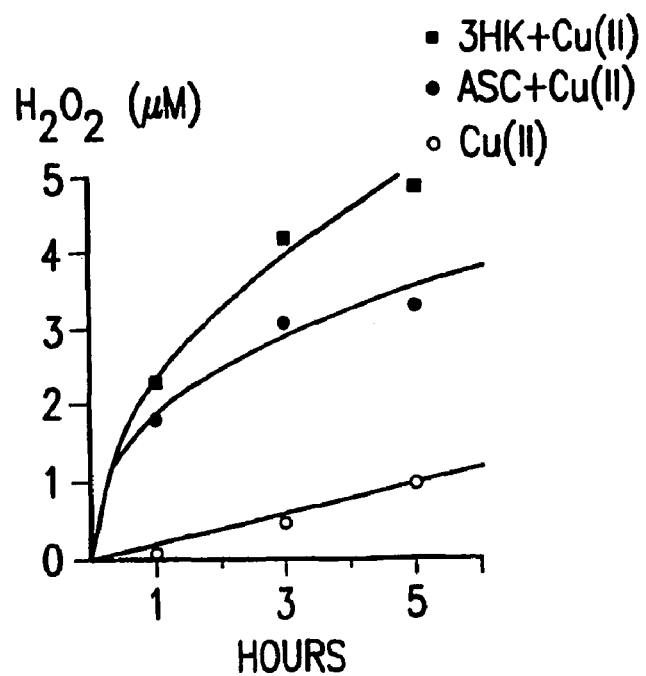

Reactions were conducted in the absence of added Cu(II), in the presence of added glycine-complexed Cu(II) (1 µM), in the presence of added glycine-complexed Cu(II) (1 µM) and catalase (1000 U/ml), or with added glycine-complexed Cu(II) (1 µM) and the copper chelator triethylenetetramine (TETA, 200 µM). The results are shown in FIGS. 4A–4C.

It was hypothesized that either a two electron transfer to dissolved molecular oxygen (in the case of 3-HK) or superoxide dismutation (in the case of 3-HAA) could result in hydrogen peroxide generation. Based on the recent observations on the Alzheimer's disease $A\beta_{1-42}$ peptide-Cu complex (Huang, X. et al., *Biochem.* 38: 7609–7616 (1999)), hydrogen peroxide production by 3-HK in the presence of Cu(II) was examined under conditions of high, ambient, and low oxygen tension (FIG. 4A). Reactions were conducted in the dark to avoid photodynamic effects. Only small amounts of hydrogen peroxide were produced by Cu(II) alone under all three oxygen tension conditions (high $O_2$:0.10 µM $H_2O_2$; ambient $O_2$:0.11 µM $H_2O_2$; low $O_2$:0.09 µM $H_2O_2$). When 3-HK was added to the incubation solution, hydrogen peroxide production was markedly increased under the high and ambient oxygen tension conditions (1.84 µM $H_2O_2$ and 1.49 µM $H_2O_2$, respectively). However, when the oxygen tension of the incubation solution was lowered by continuous argon sparging, production of hydrogen peroxide was markedly inhibited (0.35 µM $H_2O_2$), indicating that molecular oxygen dissolved in the reaction buffer is the substrate for hydrogen peroxide production.

Next, the time dependence of hydrogen peroxide generation was investigated at 37° C. in the dark. The generation of hydrogen peroxide by both 3-HK and ascorbate (ASC), the positive control, reacting with Cu(II) was continuous over five hours (FIG. 4B), indicating that neither 3-HK nor ascorbate is consumed over the time course of the present experiments. Copper may act catalytically in this situation, cycling between the reduced state (fostered by reaction with 3-HK) and the oxidized state (promoted by reaction with molecular oxygen).

Figure 4C:
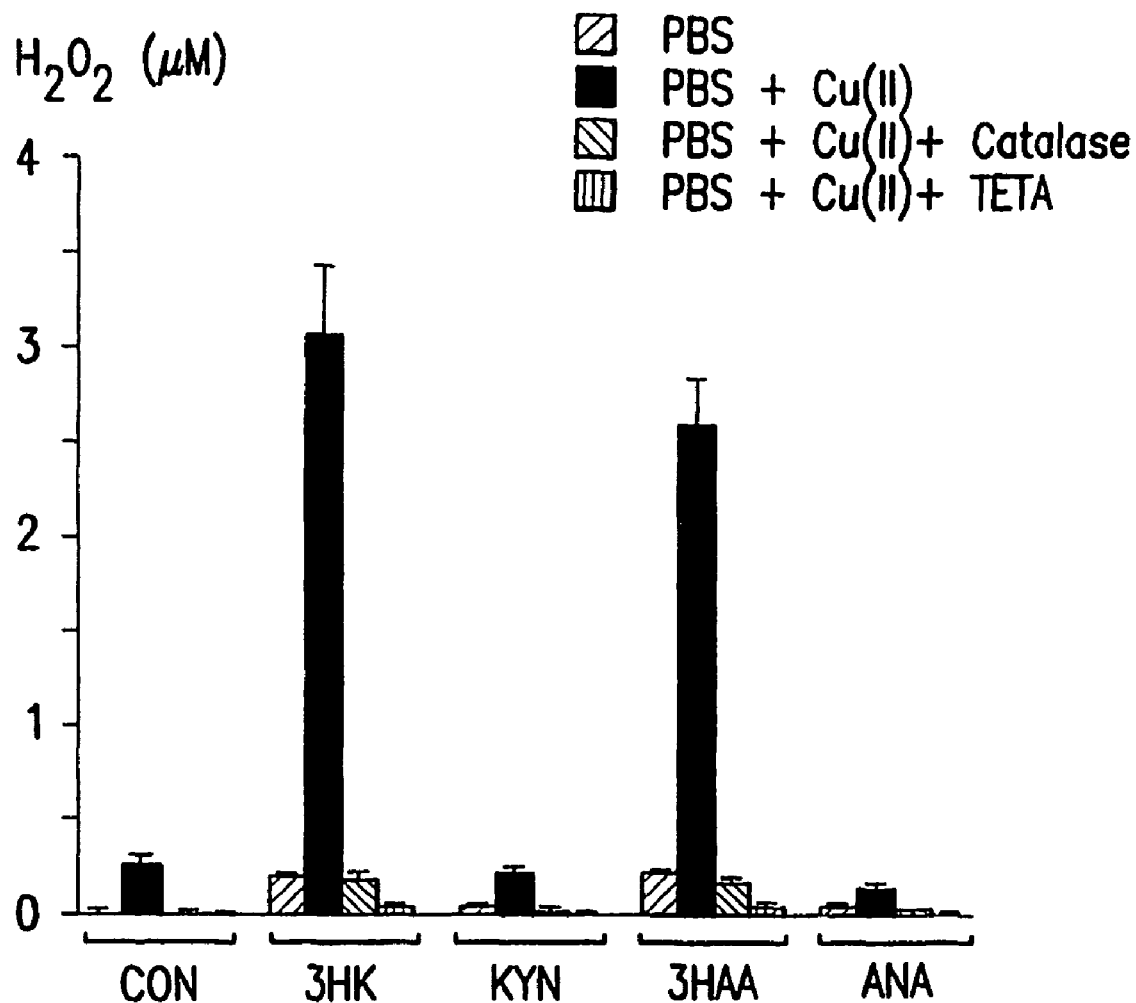

Next the metal dependence was compared to either 3-HK or 3-HAA to KYN or ANA in their ability to generate hydrogen peroxide under ambient gas conditions (FIG. 4C). Under control conditions using CHELEX™ chelating ion exchange resin-treated PBS to remove trace metal ions, no hydrogen peroxide was generated. Only a small quantity (approx. 0.3 µM) of hydrogen peroxide was generated when Cu(II) alone (1 µM) or the non-phenolic metabolites KYN or ANA were added to the CHELEX™ chelating ion exchange resin-treated PBS. However, addition of 3-HK or 3-HAA resulted in marked hydrogen peroxide generation (approx. 3 µM), which was abolished by addition of the hydrogen peroxide scavenging enzyme catalase. Hydrogen peroxide production by 3-HK or 3-HAA co-incubated with Cu(II) was also abolished by addition of the copper chelator TETA, demonstrating the metal dependence of this reaction.

Although two Fenton chemistry substrates, hydrogen peroxide and reduced redox-active metal, are produced by 3-HK and 3-HAA, evidence of the hydroxyl radical was not detected using the thiobarbituric acid-reactive substance assay (Huang, X. et al., *Biochem.* 38:7609–7616 (1999)) (data not shown). This result does not exclude the hydroxyl radical production by the reaction of 3-HK or 3-HAA and Cu(II) since it is possible that the radical may be consumed at the site of generation before it has time to react with the TBARS indicator compound.

Example 4

α-Crystallin Cross-linking Studies—Frozen stock aliquots of recombinant human $\alpha_B$-crystallin (5 mg/ml in PBS) or freshly prepared total lens protein from dissected calf lens (chilled PBS, pH 7.4, with added protease inhibitor cocktail homogenized in a ground glass tissue homogenizer and immediately frozen and stored at −80° C.) were dissolved to final concentrations of 25 µg/ml (for the experiments involving recombinant $\alpha_B$-crystallin) or 100 µg/ml (for the experiments with total lens protein). Various solutions containing 3-HK (10 µM) or other kynurenine pathway metabolites (10 µM), Cu(II)-glycine (10 µM), Fe(III)-citrate (10 µM), and triethylenetetramine (TETA, 200 µM), were added in combinations as indicated. All solutions were prepared under sterile conditions in a laminar flow tissue culture hood in a final volume of 1.0 ml sterile PBS and placed in sterile 1.5 ml translucent siliconized Eppendorf tubes. Solutions were incubated for five days at 37° C. in the dark to avoid photodynamic effects. After incubation, aliquots of the total lens protein solutions were mixed with sample buffer containing 4% SDS and 5% β-mercaptoethanol, heated to 95° C. for 5 minutes, and loaded at 1 µg/lane on a 10–20% Tricine gel (Novex, San Diego, Calif.). The gels were then electroblotted to polyvinylidene difluoride membranes using a BioRad transbiot cell, fixed, blocked, and then probed with a 1:1000 dilution of polyclonal rabbit anti-$\alpha_B$-crystallin antibody overnight at 4° C. The blot was then washed and incubated with anti-rabbit-horseradish peroxidase conjugate (Pierce, Rockford, Ill.) for 2 hours at room temperature. Chemiluminescent detection was carried out using SuperSignal Ultra (Pierce, Rockford, Ill.) according to the manufacturer's instructions. For the experiments with recombinant $\alpha_B$-crystallin, aliquots of the protein solutions were mixed with sample running buffer containing NuPAGE sample buffer (Novex, San Diego, Calif.) and 10% β-mercaptoethanol, heated to 95° C. for 5 minutes, spun briefly, then loaded on a NuPAGE 4–12% Bis-Tris polyacrylamide gel at 375 ng/lane and electrophoresed with denaturing 3-(N-morpholino)propanesulfonic acid (MOPS)-SDS running buffer according to the manufacturer's recommendations. Gels were stained for total protein using Bio-Rad Silver Stain Plus® (Hercules, Calif.) according to the manufacturer's recommendation. The results are shown in FIGS. 5, 6A, 6B and 7.

Figure 5:
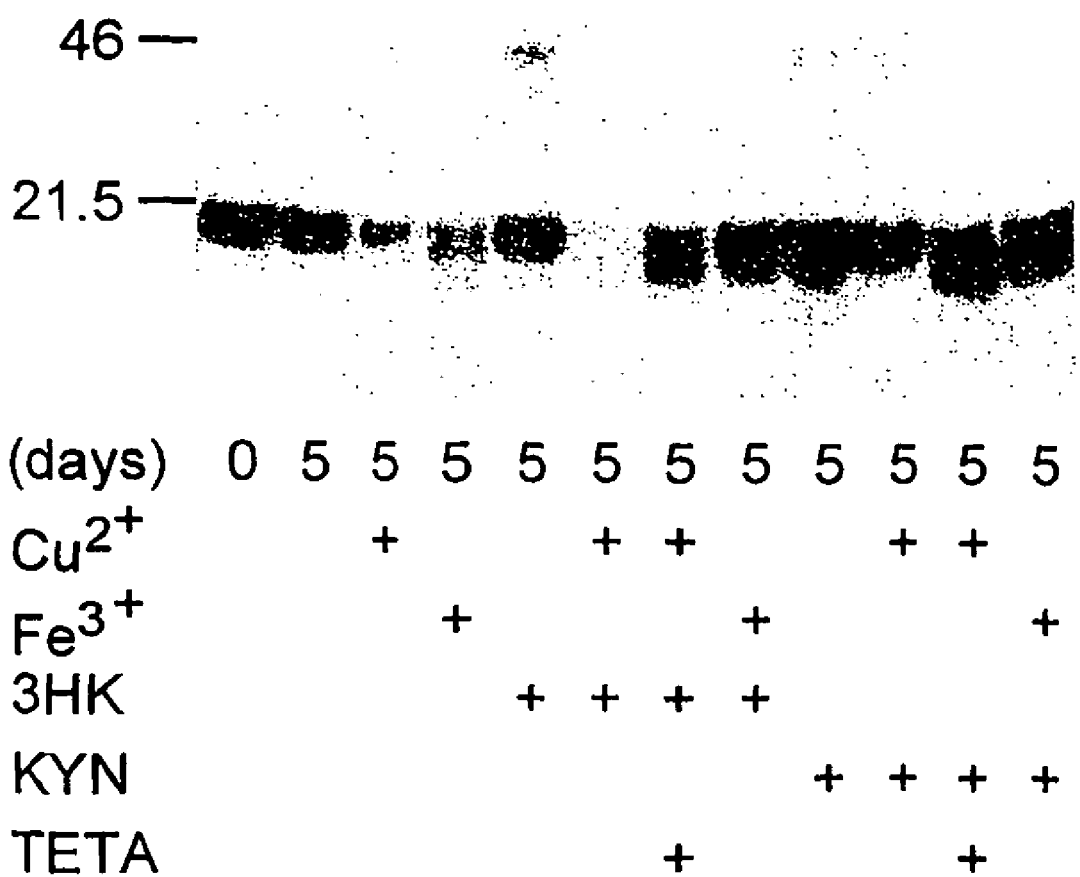
FIG. 5: Western blot analysis of α-crystallin incubation in the presence of glycinated Cu(II) (10 µM), Fe(III) (10 µM), the Cu(II) chelator TETA (200 µM), L-kynurenine (10 µM), and 3-hydroxykynurenine (10 µM). Molecular weight markers are noted on the left of the panel. A control sample (first lane) of total lens protein was prepared and immediately frozen until the assay.

Because 3-HK, hydrogen peroxide and copper co-localize with α-crystallin in the lens, the interaction of 3-HK and 3-HAA with total calf lens proteins in the presence or absence of Cu(II) was determined. In these experiments, $\alpha_B$-crystallin migration was monitored by Western blot analysis. The incubations were conducted in the dark to avoid photodynamic effects. When 3-HK was added to the incubation mixture, formation of SDS- and β-mercaptoethanol resistant apparent dimers and higher order oligomers were observed (FIG. 5). The 3-HK induced $\alpha_B$-crystallin cross-linking effect was dramatically enhanced in the presence of Cu(II) (10 µM) and was abolished by co-incubation with the copper chelator TETA. The apparent $\alpha_B$-crystallin cross-linking promoted by co-incubation of 3-HK with Cu(II) was also accompanied by loss of the monomeric protein species and generation of smaller protein fragments (<approx. 20 kD). Addition of the copper chelator TETA reversed the depletion of monomeric $\alpha_B$-crystallin when this protein was co-incubated with 3-HK and Cu(II). The presence of some apparent cross-linking observed with 3-HK in the absence of added Cu(II) may be due to interaction with trace Cu(II) present in the incubation solution since the buffer solutions, even after careful treatment with CHELEX™-100 chelating ion exchange resin, still contain approximately 0.1 µM total Cu background contamination as measured by inductively-coupled plasma mass spectroscopy (data not shown).

The Western blot results also indicated that incubation with the non-phenolic 3-HK analog, KYN, does not induce $\alpha_B$-crystallin cross-linking, consistent with the lack of activity in the assays for metal reduction, superoxide generation, and hydrogen peroxide production. Cross-linking of $\alpha_B$-crystallin did not occur when Fe(III) was substituted for Cu(II). Similar results were obtained when the Western blots were probed for $\alpha_A$-crystallin (data not shown).

Figure 6A:
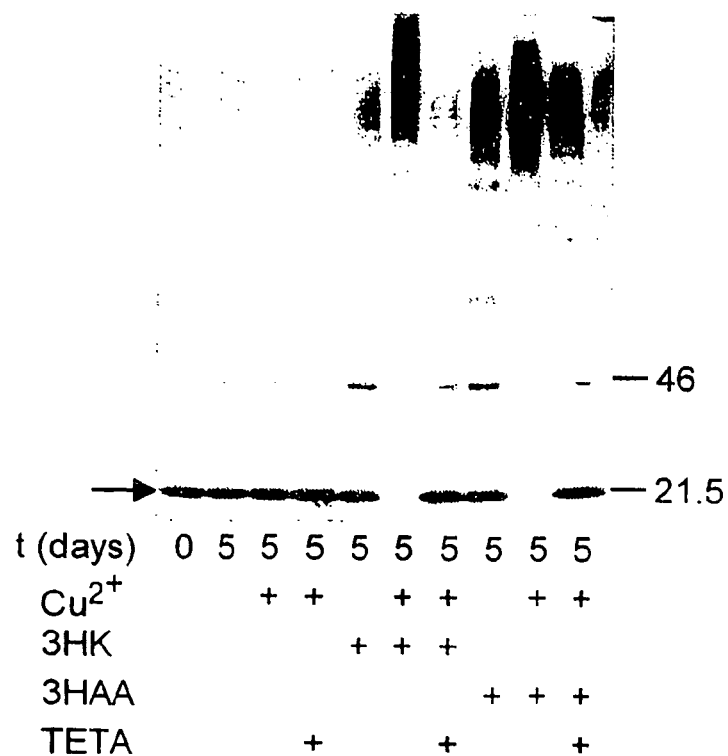
FIGS. 6A & 6B: silver staining for total protein after SDS-polyacrylamide gel electrophoresis of purified recombinant human $\alpha_B$-crystallin (FIG. 6A) or bovine serum albumin (FIG. 6B) after incubation in the presence of glycinated Cu(II) (10 µM), the Cu(II) chelator TETA (200 µM), 3-hydroxykynurenine (10 µM), and 3-hydroxyanthranilic acid (10 µM). Molecular weight markers are noted on the right of the panels. A control sample (first lane) of total lens protein was prepared and immediately frozen until the assay. Arrowhead marks monomeric species.

To exclude the effects of other lens proteins on the observed findings in FIG. 5, these interactions with purified recombinant human $\alpha_B$-crystallin were examined. After 5 days of incubation at 37° C. in the dark, $\alpha_B$-crystallin was predominantly present as a monomer, even when co-incubated with Cu(II) (FIG. 6A). However, after incubation with 3-HK, apparent dimeric and higher order oligomers were observed (FIG. 6A). After co-incubation with Cu(II) and 3-HK together, the monomeric and apparent dimeric $\alpha_B$-crystallin species were depleted and a prominent high molecular weight smear was observed. This effect was substantially attenuated by the copper chelator TETA. Addition of TETA completely reversed the depletion of monomeric $\alpha_B$-crystallin when incubated with 3-HK and Cu(II).

Figure 7:
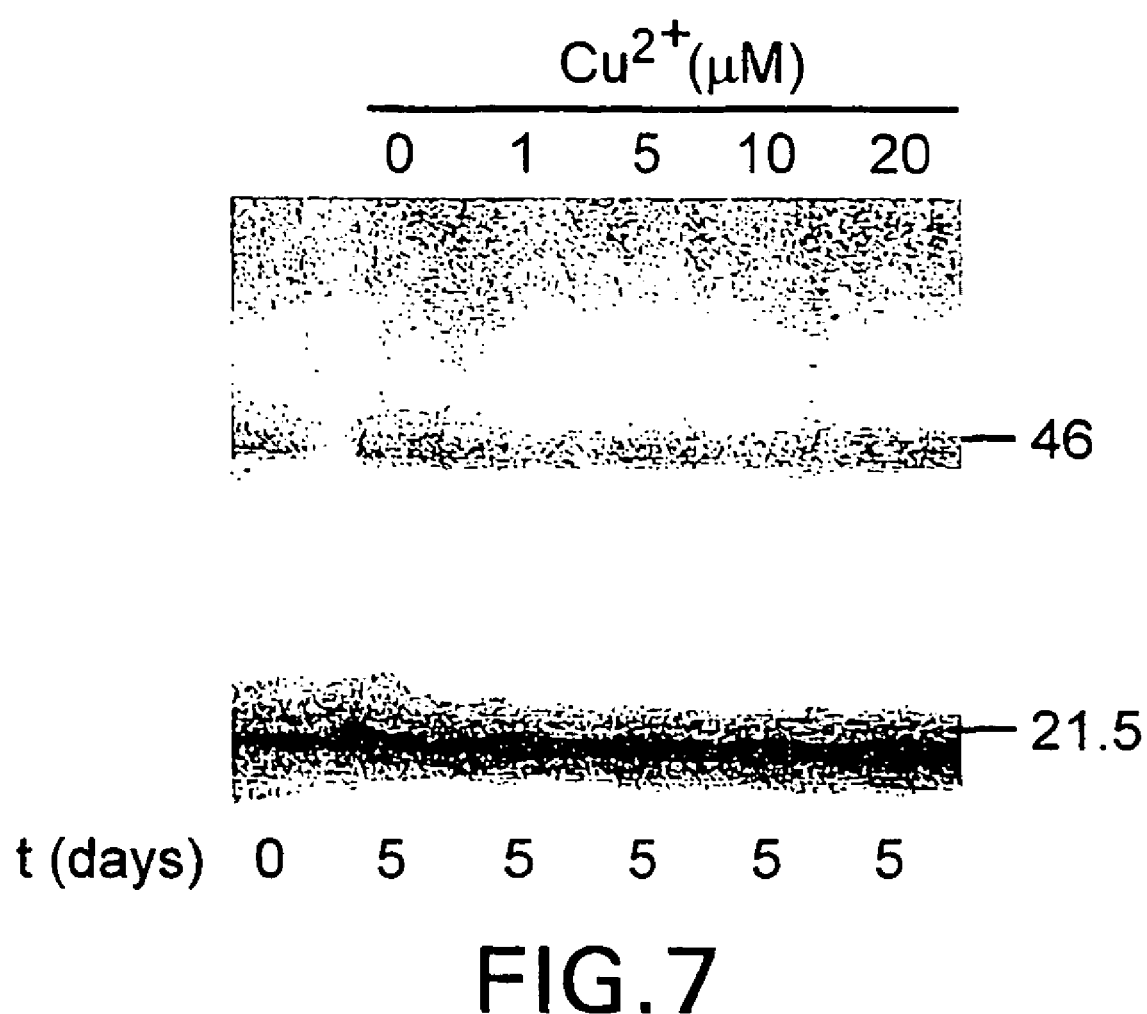
FIG. 7: silver staining for total protein after SDS-polyacrylamide gel electrophoresis of recombinant human $\alpha_B$-crystallin after incubation in the presence of various micromolar concentrations of glycinated Cu(II). Molecular weight markers are noted on the right of the panel. A control sample (first lane) of total lens protein was prepared and immediately frozen until the assay.

Interactions with 3-HAA produced a similar pattern of Cu(II)-dependent apparent oligomerization and loss of the monomer which was reversed with TETA. Mass spectroscopy analysis of the products observed by electrophoresis and silver staining confirmed the presence of covalently cross-linked oligomers which matched the Western blot (data not shown). Incubation of recombinant $\alpha_B$-crystallin with varying concentrations of Cu(II) alone did not result in observable apparent cross-linking or degradation (FIG. 7).

Figure 6B:
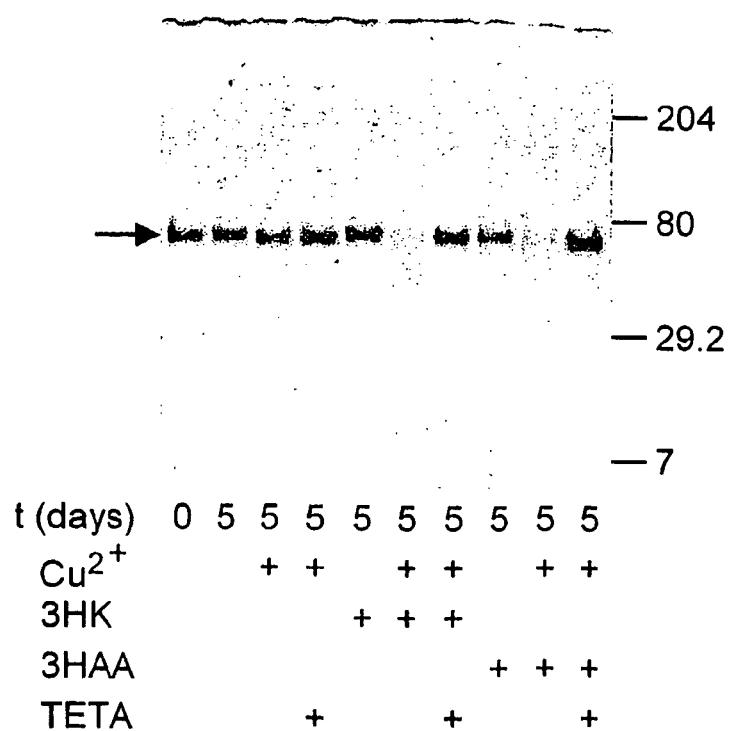

The interaction of 3-HK and 3-HAA with Cu(II) in the presence of another target protein, bovine serum albumin (BSA) (25 µg/1 ml) (FIG. 6B) was then compared. After 5 days of incubation at 37° C. in the dark, BSA was predominantly present as a monomer, even when co-incubated with Cu(II) (FIG. 6B). In contrast to the findings with $\alpha_B$-crystallin, apparent dimeric and higher order oligomers after incubation with 3-HK alone were not observed. After co-incubation of 3-HK with Cu(II), the monomer was depleted without emergence of apparent detectable cross-linked species. A faint smear was dectectable between approximately 30 kD and 60 kD which may represent fragmentation of the BSA monomer. The protein depletion effect was abolished by the copper chelator TETA. Interactions with 3-HAA produced a similar pattern of apparent Cu(II)-dependent protein depletion. A similar pattern of protein depletion was observed when myelin basic protein was used as a target protein (data not shown). Thus, the oxidative cross-linking induced by 3-HK and 3-HAA in the presence of Cu(II) was specific for α-crystallin when compared to BSA and myelin basic protein.

Since the Fenton chemistry substrates hydrogen peroxide and reduced redox-active metal are generated by 3-HK and 3-HAA, it was hypothesized that the cross-linking of $\alpha_B$-crystallin might be mediated by generation of the hydroxyl radical. However, incubation of $\alpha_B$-crystallin with either 3-HK or 3-HAA and Cu(II) in the presence of hydroxyl radical scavenging agents such as DMSO, mannitol, or salicylate did not inhibit the cross-linking of $\alpha_B$-crystallin (data not shown). Similarly, neither catalase nor superoxide dismutase were capable of inhibiting the cross-linking of $\alpha_B$-crystallin by 3-HK or 3-HAA in the presence of Cu(II) (data not shown).

Example 5

Studies of Tanned Calf Lens Crystalin in Assay of Crystallin Protein for Metal Reduction Capacity—α-Crystallin (10 mg/ml) from calf lens was modified by reaction with 3-HK (100 µM), 3-HAA (100 µM), or ASC (100 µM) in PBS, ph 7.4, for 12 hours at 4° C. in the dark. Control samples were incubated with ascorbic acid (100 µM) or without added reductant. The tanning incubation solutions also contained triethylenetetramine (TETA, 200 µM) to prevent cross-linking of the protein. After incubation, free reductant was removed from the tanned α-crystallin preparations by exhaustive dialysis at 4EC in the dark utilizing PBS, pH 7.4, containing CHELEX™ 100 chelating ion exchange resin (BioRad, Hercules, Calif.). The various modified α-crystallin preparations (100 µg/ml) were coincubated with either Cu(II)-glycine glycine (25 µM) or Fe(III)-citrate (25 µM) for one hour at 37° C. and assayed for metal reduction capacity using the BC and BP spectrophotometric assay as detailed above. Incubated and dialyzed α-crystallin (100 µg/ml) and untreated α-crystallin (100 µg/ml) preparations were used for procedural control.

Figure 8:
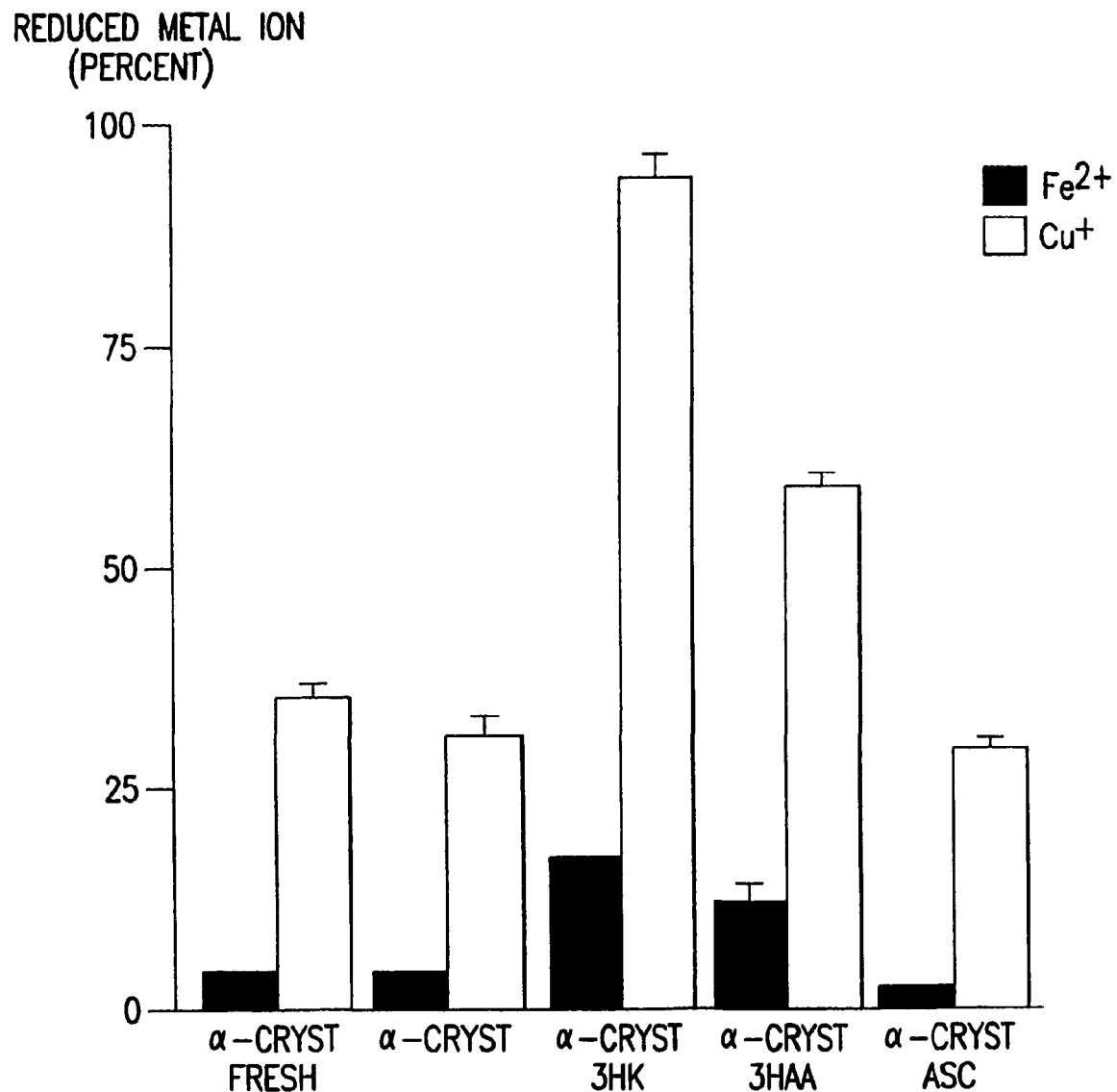
FIG. 8: graph illustrating the results of α-crystallin testing for metal reduction capacity wherein α-crystallin is incubated with various kynurenine metabolites after the removal of free metabolite by dialysis. Controls are fresh α-crystallin and unmodified α-crystallin treated in the absence of added metabolite. Values represent the means±SD, for three independent measurements.

In summary, in these preparations, α-crystallin was incubated with the various kynurenine metabolites, then free metabolite was removed by dialysis and the resulting "tanned" α-crystallin was tested for metal reduction capacity. α-Crystallin reduced approximately 35% of the available Cu(II) and a negligible percentage of Fe(III). 3-HK: α-crystallin reduced nearly 100% of the available Cu(II) and approximately 20% of the available Fe(III). 3-HAA: α-crystallin reduced approximately 65% of the available Cu(II). Importantly, treatment of α-crystallin with ascorbate, a potent metal reducing agent, did not result in the enhancement of α-crystallin reducing efficiency (FIG. 8).

Example 6

Superoxide Assay—The fluorometric assay for superoxide is based upon the dihydroethidium (DHE, HYDROETHDNE™) method (Molecular Probes, Eugene, Oreg.) and used according to the manufacturer's instructions. DHE (1 mM) was freshly prepared in 100% argon-sparged DMSO. The reaction solutions were carried out in PBS, pH 7.4, under ambient gas conditions, in 96-well format plates and contained a test compound (KYN, 3-HK, 3-HAA, and ANA, each at 10 µM), DHE (100 µM), +/− Cu(II)-glycine (1 µM) and incubated at 37EC for 60 minutes. Reactions were conducted in the dark to avoid photodynamic effects. Abolition of the reading by co-incubation with superoxide dismutase (1000 U/ml) was used for establishing superoxide specificity. The fluorescent readings were recorded by a Packard FLUOROCOUNT™ fluorescent plate reader with a 510 nm excitation filter and 590 nm emission filter. Potassium superoxide dissolved in degassed DMSO was used as a positive control.

Figure 9:
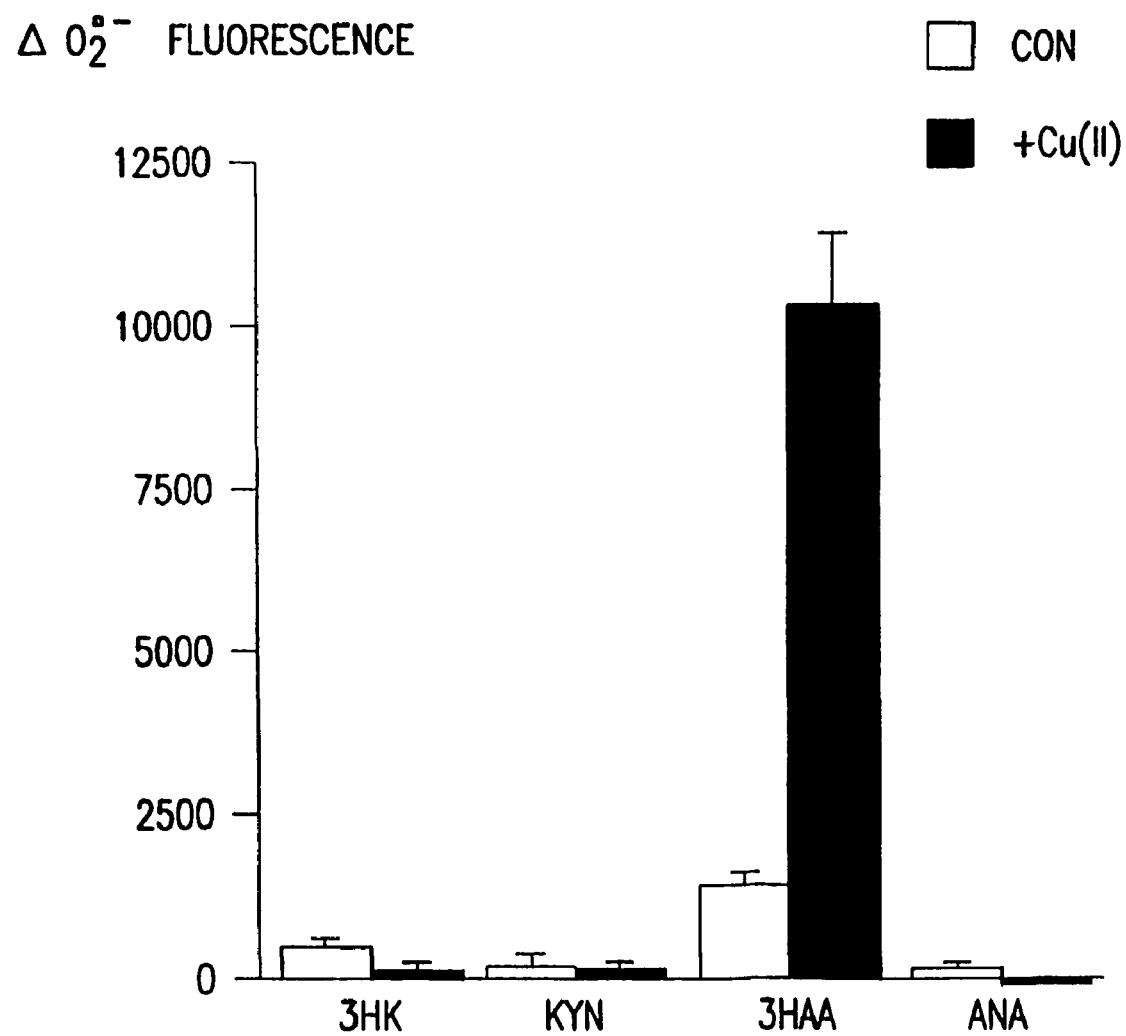
FIG. 9: graph illustrating the results of a fluorometric assay for superoxide wherein the presence of Cu(II) increased production of superoxide by 3-HAA, but not 3-HK, KYN or ANA. Fluorescence values represent the difference between samples incubated with and without superoxide dismutase (SOD, 1000 U/ml). In all cases, addition of SOD lowered the fluorescence value to baseline. Values represent the mean±SD for three independent measurements.

This example examines whether superoxide is generated by the reaction of 3-HK and 3-HAA with Cu(II) under ambient oxygen tension conditions (FIG. 9). It was found that significant superoxide production by 3-HAA was removed by superoxide dismutase. Superoxide production by 3-HK, KYN, and ANA was negligible. Superoxide generation by 3-HAA was strongly promoted by the presence of Cu(II) which, in contrast, did not promote superoxide production by 3-HK, KYN, or ANA.

Example 7

Screening Assay for Agents Useful in the Treatment or Prevention of Cataracts—The following components are added in the order indicated to a 1.5 ml siliconized Eppendorf tube: PBS (with $Ca^{2+}/Mg^{2+}$), 25 µM redox-active metal, 50 µM test agent (- test agent control), 10 µM kynurenine pathway metabolite, and lens protein at an appropriate concentration (5–500 µg/ml) for accurate analysis or visualization after gel electrophoresis or other assay procedure for detecting separating cross-linked from non-cross-linked lens protein. Cu(II) is prepared as a glycinated complex (1:6). Fe(III) is prepared as a citrated complex (1:6). Redox-active metals are present at a final concentration of about 1–25 µM. The test agent is present at a final concentration ranging from about 10–200 µM. Kynurenine pathway metabolites are selected from the group consisting of 3-hydroxykynurenine, 3-hydroxyanthranilic acid, xanthurenic acid, and other o-aminophenol compounds, and are present at a final concentration of about 1–25 µM. A non-hydroxylated metabolite at the same concentration may be substituted as a negative control. The lens protein may be recombinant or purified crystallins (about 10–50 µg/ml). Total lens protein may be at a final concentration of about 50–500 µg/ml.

The mixture is incubated at 37° C. for about 1–10 days in the dark and/or under UVB irradiation (polymerization and fragmentation of lens proteins are significantly accelerated under UVB irradiation at approximately 365 nm, approximately 1920 µW/cm$^2$)). The mixture is mixed gently by inversion daily. At the end of the incubation period, Western blot of a 10 µl of the incubation mixture is carried out by conducting SDS-PAGE, transfer to nitrocellulose, probing with an appropriate antibody (a primary antibody, e.g., rabbit anti-$\alpha_A$-crystallin or anti-$\alpha_B$-crystallin) followed by appropriate secondary antibody and visualization by chemiluminescence. Molecular weight markers centered on about 20–50 kD are included (α-crystallin monomer is approximately 20 kD).

Positive result for a test agent is revealed by blocking (ie., absence or diminution) of polymerization smears and fragmentation bands, as well as an intensification of the monomer and lower order oligomer products. Minimum controls for comparison include the incubation mixture without the test agent and the lens protein in the absence of active kynurenine metabolites and/or redox-active metals.

Use of a complete series of controls, as listed below, enables a determination of the requirement for each of the key assay components and their relative contribution alone and in the functional combinations listed:

1. Protein-fresh frozen.
 2. Protein alone.
 3. Protein in the presence of metal(s).
 4. Protein in the presence of active kynurenine pathway metabolite.
 5. Protein in the presence of metal and active metabolite.
 6. Protein in the presence of inactive kynurenine metabolite.
 7. Protein in the presence of metal and inactive kynurenine metabolite.
 8. Protein in the presence of test agent alone.

9. Protein in the presence of test agent and metal.
10. Protein in the presence of test agent and active kynurenine metabolite.
11. Protein in the presence of test agent and inactive kynurenine metabolite.

Controls 1 and 2 illustrate the profile of the target protein alone. Control 3 indicates the activity dependent upon metal ion alone. Control 4 indicates activity dependent upon active kynurenine metabolite alone. Control 5 indicates the activity dependent upon metal and active kynurenine metabolite. Controls 6 and 7 repeat metal dependency when inactive kynurenine metabolites are present. Control 8 measures change in lens cross-linking caused by test agent alone. Control 9 measures metal and test agent effect on cross-linking of lens protein. Controls 10 and 11 measure the effect on cross-linking dependent upon test agent and either active or inactive kynurenine metabolite. Differences between the controls and the complete assay mixture determine the synergy or increased effect which is dependent upon all assay components being present with the test agent.

Example 8

Screening Assay for Agents Causing or Accelerating Cataract Formation—The following components are added in the order indicated to a 1.5 ml siliconized Eppendorf tube: PBS (with $Ca^{2+}/Mg^{2+}$), 25 µM redox-active metal, 50 µM test agent (- test agent control), 10 µM kynurenine pathway metabolite, and lens protein at an appropriate concentration. Cu(II) is prepared as a glycinated complex (1:6). Fe(III) is prepared as a citrated complex (1:6). Redox-active metals are present at a final concentration of about 1–25 µM. The test agent to be screened is present at a final concentration ranging from about 10–200 µM. Kynurenine pathway metabolites are selected from the group consisting of 3-hydroxykynurenine, 3-hydroxyanthranilic acid, xanthurenic acid, and other o-aminophenol, and are present at a final concentration of about 1–25 µM. A non-hydroxylated metabolite at the same concentration may be substituted as a negative control. The lens protein may be recombinant or purified crystallins (about 10–50 µg/ml). Total lens protein may be at a final concentration of about 50–500 µg/ml.

The mixture is incubated at 37° C. for about 1–10 days in the dark and/or under UVB irradiation (polymerization and fragmentation of lens proteins are significantly accelerated under UVB irradiation). The mixture is mixed gently by inversion daily. At the end of the incubation period, Western blot of a 10 µl of the incubation mixture is carried out by conducting SDS-PAGE, transfer to nitrocellulose, probing with an appropriate antibody (a primary antibody, e.g., rabbit anti-$\alpha_A$-crystallin or anti-$\alpha_B$-crystallin) followed by appropriate secondary antibody and visualization by chemiluminescence. Molecular weight markers centered on about 20–50 kD are included ($\alpha$-crystallin monomer is approximately 20 kD).

Positive result for a test agent is revealed by promoting (ie., increasing or accelerating) polymerization smears and fragmentation bands, as well as an intensification of the dimer and higher order oligomer products. Controls for comparison include the incubation mixture without the test agent and the lens protein in the absence of active kynurenine metabolites and/or redox-active metals.

A decrease in the amount of dimer and higher order oligomer products indicates that the test agent inhibits cataract formation and may be used as a therapeutic product to treat or to inhibit cataracts. Alternatively, an increase in the amount of dimer and higher order oligomer products indicates that the test agent promotes cataract formation and therefore, that human and animal contact and ingestion should be avoided. As in Example 6, the same controls may be run in this example to determine the activity dependent upon the listed reactants, except here the assay anticipates an increase in cross-linking rather than a decrease in lens protein cross-linking.

Example 9

Method of Treating Age-Related Cataracts (ARC) with Clioquinol—Clioquinol can be used for the treatment of ARC either with eye-drops or taken orally as a tablet, or introduced as a skin ointment, by injection, by suppository or by any other form where clioquinol may enter the blood stream or eye. The eye-drops are the preferred method.

If the eye-drops are employed, then, preferably, the eye drop solution consists of a 0.1–40 micromolar, preferably ten micromolar, solution in neutral buffered saline, but can vary in pH from 5–8 in isotonic saline. One to six, preferably three, drops are delivered one to six, preferably three, times a day, for one week to two years, preferably six months, possibly indefinitely in cases where prevention is required.

If an oral tablet is employed, then the tablets contain 10–1000 mg clioquinol, preferably 125 mg, and one to four of the tablets are taken one to six times a day for one week to two years, preferably for six months, or possibly indefinitely in cases where prevention is required.

Having now fully described this invention, it will be understood by those of skill in the art that it can be performed within any wide range of equivalent modes of operation as well as other parameters without affecting the scope of the invention or any embodiment thereof.

All patents and publications cited in the present specification are incorporated by reference herein in their entirety.

What is claimed is:

1. A method for the identification of a candidate pharmacological agent that results in the prevention of or reduction in cross-linking of a target protein, said method comprising:
   (a) adding a reducible redox-active metal source to a first sample of the target protein comprising an auto-oxidizing kynurenine pathway metabolite;
   (b) allowing said first sample to incubate for an amount of time sufficient to allow cross-linking of said target protein;
   (c) adding said reducible redox-active metal source to a second sample of the target protein comprising an auto-oxidizing kynurenine pathway metabolite, said second sample additionally comprising a candidate pharmacological agent;
   (d) allowing said second sample to incubate for the same amount of time as said first sample;
   (e) determining the amount of target protein cross-linking by said first sample and said second sample; and
   (f) comparing the amount of target protein cross-linking produced by said first sample to the amount of target protein cross-linking produced by said second sample;
   whereby a decrease in the amount of target protein cross-linking produced by said second sample, as compared to said first sample, indicates that said candidate pharmacological agent is useful in the treatment of cataracts.

2. The method of claim 1, wherein the amount of cross-linked target protein in said first and said second sample is determined by a method selected from the group consisting of: Western blotting, filtration assay, aggregation/sedimentation, turbidometry, fluorometry, spectrophotometry, and lens or retinal culture combined with light microscopy or light scattering technology.

3. The method of claim 1, wherein said target protein is α-crystallin.

4. The method of claim 1, wherein said reducible redox-active metal source comprises Cu(II).

5. The method of claim 1, wherein said reducible redox-active metal source comprises Fe(III).

6. The method of claim 1, wherein said auto-oxidizing kynurenine pathway metabolite is an o-aminophenol compound.

7. The method of claim 6, wherein said o-aminophenol compound is selected from the group consisting of: 3-hydroxykynurenine, 3-hydroxyanthranilic acid, and xanthurenic acid.

8. The method of claim 7, wherein said o-aminophenol compound is 3-hydroxykynurenine.

9. The method of claim 7, wherein said o-aminophenol compound is 3-hydroxyanthranilic acid.

10. The method of claim 1, wherein said second sample comprises two or more different candidate pharmacological agents.

11. The method of claim 1, wherein said first and second samples are incubated under ultraviolet B irradiation.

12. An assay method for determining whether a candidate agent causes or accelerates the cross-linking of a target protein, wherein an increase in target protein cross-linking indicates potential cataract formation, said method comprising:
   (a) adding a reducible redox-active metal source to a first sample of the target protein comprising an auto-oxidizing kynurenine pathway metabolite;
   (b) allowing said first sample to incubate for an amount of time sufficient to allow cross-linking of said target protein;
   (c) adding said reducible redox-active metal source to a second sample of the target protein comprising an auto-oxidizing kynurenine pathway metabolite, said second sample additionally comprising a candidate agent;
   (d) allowing said second sample to incubate for the same amount of time as said first sample;
   (e) determining the amount of target protein cross-linking by said first sample and said second sample; and
   (f) comparing the amount of target protein cross-linking produced by said first sample to the amount of target protein cross-linking produced by said second sample;
   whereby an increase in the amount of target protein cross-linking produced by said second sample, as compared to said first sample, indicates that said agent may cause or accelerate the formation of cataracts.

13. The method of claim 12, wherein the amount of cross-linked target protein in said first and said second sample is determined by the method selected from the group consisting of: Western blotting, filtration assay, aggregation/sedimentation, turbidometry, fluorometry, spectrophotometry, and lens or retinal culture combined with light microscopy or light scattering technology.

14. The method of claim 12, wherein said target protein is α-crystallin.

15. The method of claim 12, wherein said reducible redox-active metal source comprises Cu(II).

16. The method of claim 12, wherein said reducible redox-active metal source comprises Fe(II).

17. The method of claim 12, wherein said auto-oxidizing kynurenine pathway metabolite is an o-aminophenol compound.

18. The method of claim 17, wherein said o-aminophenol compound is selected from the group consisting of: 3-hydroxykynurenine, 3-hydroxyanthranilic acid, and xanthurenic acid.

19. The method of claim 18, wherein said o-aminophenol compound is 3-hydroxykynurenine.

20. The method of claim 18, wherein said o-aminophenol compound is 3-hydroxyanthranilic acid.

21. The method of claim 12, wherein said second sample comprises two or more different candidate agents.

22. The method of claim 12, wherein said first and samples are incubated under ultraviolet B irradiation.

* * * * *